(12) United States Patent
Hungenberg et al.

(10) Patent No.: US 8,497,228 B2
(45) Date of Patent: Jul. 30, 2013

(54) ACTIVE SUBSTANCE COMBINATIONS WITH INSECTICIDAL AND ACARICIDAL PROPERTIES

(75) Inventors: Heike Hungenberg, Langenfeld (DE);
Peter Jeschke, Bergisch Gladbach (DE);
Robert Velten, Langenfeld (DE);
Rüduger Fischer, Pulheim (DE);
Wolfgang Thielert, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 435 days.

(21) Appl. No.: 12/676,462

(22) PCT Filed: Aug. 26, 2008

(86) PCT No.: PCT/EP2008/006970
§ 371 (c)(1),
(2), (4) Date: Mar. 4, 2010

(87) PCT Pub. No.: WO2009/030399
PCT Pub. Date: Mar. 12, 2009

(65) Prior Publication Data
US 2010/0210459 A1 Aug. 19, 2010

(30) Foreign Application Priority Data
Sep. 5, 2007 (EP) ..................................... 07115755

(51) Int. Cl.
*A01N 41/10* (2006.01)
*A01N 43/40* (2006.01)
*A01N 43/60* (2006.01)
*A01N 43/78* (2006.01)

(52) U.S. Cl.
USPC ............ 504/100; 514/336; 514/365; 514/616

(58) Field of Classification Search
USPC .................................. 514/336, 616; 504/100
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 5,876,739 A | 3/1999 | Turnblad et al. | |
| 2003/0176428 A1 | 9/2003 | Schneidersmann et al. | |
| 2008/0280953 A1* | 11/2008 | Gorgens et al. | 514/336 |
| 2009/0253749 A1* | 10/2009 | Jeschke et al. | 514/336 |

FOREIGN PATENT DOCUMENTS

| | | |
|---|---|---|
| DE | 10 2004 047 922 A1 | 4/2006 |
| DE | 10 2006 014 482 A1 | 10/2007 |
| EP | 0 539 588 A1 | 5/1993 |
| EP | 1 006 107 A2 | 6/2000 |
| EP | 1 782 689 A2 | 5/2007 |
| JP | 5-4966 | 1/1993 |
| WO | 0228186 | 4/2002 |
| WO | 02080675 | 10/2002 |
| WO | WO 2006/037475 * | 4/2006 |
| WO | 2007/115643 A1 | 10/2007 |
| WO | 2007/115644 A1 | 10/2007 |
| WO | 2007/115646 A1 | 10/2007 |

OTHER PUBLICATIONS

Hackh's Chemical Dictionary, 4th ed., McGraw-Hill Book Co., New York, 1977, p. 170.*
S.R.Colby "Weeds", British Library, 1967(15): 20-22.
International Search Report based on European application No. PCT/EP2008/006970 dated Aug. 26, 2008.

* cited by examiner

*Primary Examiner* — John Pak
(74) *Attorney, Agent, or Firm* — Baker Donelson Bearman Caldwell & Berkowitz, PC

(57) ABSTRACT

The present invention relates to novel active substance combinations which contain firstly at least one known compound of the formula (I)

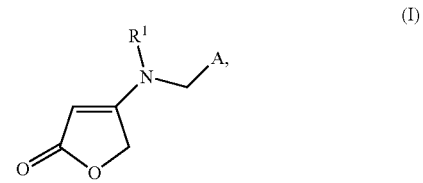

in which
R¹ and A have the meanings given in the description,
and secondly at least one further known active substance from the class of the phthalic diamides, and which are highly suitable for controlling animal pests such as insects and undesired acarids.

14 Claims, No Drawings

ACTIVE SUBSTANCE COMBINATIONS WITH INSECTICIDAL AND ACARICIDAL PROPERTIES

CROSS REFERENCE TO RELATED APPLICATIONS

This application is a §371 National Stage Application of PCT/EP2008/006970 filed Aug. 26, 2008, which claims priority to European Application 07115755.6 filed Sep. 5, 2007.

BACKGROUND OF THE INVENTION

1. Field of the Invention

The present invention relates to novel active substance combinations which contain firstly at least one known compound of the formula (I) and secondly at least one further known active substance from the class of the phthalic diamides, and which are highly suitable for controlling animal pests such as insects and undesired acarids. The invention also relates to methods of controlling animal pests on plants and seed, to the use of the active substance combinations according to the invention for the treatment of seed, to a method of protecting seed, and, finally, to the seed treated with the active substance combinations according to the invention.

2. Description of Related Art

On page 3, before the line that states, "It is the object of the invention to satisfy one or more of the abovementioned requirements, such as,", please insert the following heading:

SUMMARY OF THE INVENTION

It has already been disclosed that compounds of the formula (I)

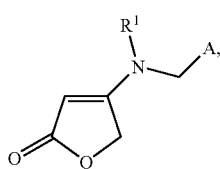

(I)

in which
A represents pyrid-2-yl or pyrid-4-yl, or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl, or represents pyrazin-3-yl or represents 2-chloropyrazin-5-yl or represents 1,3-thiazol-5-yl which is optionally substituted in the 2-position by chlorine or methyl, or
A represents a radical pyrimidinyl, pyrazolyl, thiophenyl, oxazolyl, isoxazolyl, 1,2,4-oxa-diazolyl, isothiazolyl, 1,2,4-triazolyl or 1,2,5-thiadiazolyl, which radical is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine),
or
A represents a radical

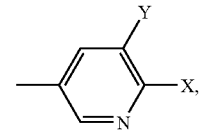

in which
X represents halogen, alkyl or haloalkyl,
Y represents halogen, alkyl, haloalkyl, haloalkoxy, azido or cyano, and
$R^1$ represents alkyl, haloalkyl, alkenyl, haloalkenyl, alkynyl, cycloalkyl, cycloalkylalkyl, halocycloalkyl, alkoxy, alkoxyalkyl, or halocycloalkylalkyl,
are insecticidally active (cf. EP 0 539 588, WO 2007/115644, WO 2007/115643, WO 2007/115646).

EP-A-1 006 107 discloses that various compounds from the class of the phthalic diamides such as, for example, flubendiamide can be used as insecticides in the crop protection sector. The insecticidal activity of various optically active phthalic diamide compounds is described in EP-A-1 782 689.

The activity of the insecticidal compound of the formula (I), and of the compound from the class of the phthalic diamides, is generally good. However, they do not always satisfy the requirements of agricultural practice, in particular at low application rates and in the case of specific pests, and there still exists a need for an economically efficient and ecologically harmless pest control.

Further demands which insecticidal compounds must meet include the reduction of the dosage rate; a substantial widening of the spectrum of pests to be controlled, including resistant pests; increased safety of use; reduced toxicity to plants and therefore better plant tolerance; the control of the pests in their various developmental stages; better behaviour during the preparation of the insecticidal compounds, for example during grinding or mixing, during their storage or during their use; a very advantageous biocidal spectrum even at low concentrations, combined with good tolerance by warm-blooded species, fish and plants; and achieving an additional effect, for example an algicidal, anthelmintic, ovicidal, bactericidal, fungicidal, molluscicidal, nematicidal, plant-activating, rodenticidal or virucidal effect.

Further specific requirements which insecticidal compounds used on vegetative and generative plant propagation material must meet include a negligible phytotoxicity when used on the seed and the plant propagation material, a compatibility with soil conditions (for example as regards the locking-up of the compound in the soil), a systemic activity in the plant, no negative effect on germination, and an activity during the life cycle of the pest in question.

It is the object of the invention to satisfy one or more of the abovementioned requirements, such as, for example, reducing the dosage rate, widening the spectrum of pests which can be controlled, including resistant pests, and, in particular, the specific requirements regarding the applicability to vegetative and generative plant propagation material.

It has now been found that combinations of at least one compound of the formula (I) and at least one phthalic diamide compound selected among flubendiamides or an optically active phthalic diamide, namely (S)-3-iodo-$N^1$-{2-methyl-4-[1,2,2,2-tetrafluoro-1-(trifluoromethyl)ethyl]phenyl}-$N^2$-(1-methyl-2-methylsulphonylethyl)phthalamide, of the formula (IIa), (S)-3-chloro-$N^1$-{2-methyl-4-[1,2,2,2-tetrafluoro-1-(trifluoromethyl)ethyl]phenyl}-$N^2$-(1-methyl- 2-methylsulphonylethyl)phthalamide, of the formula (IIb), (S)-3-bromo-N¹-{2-methyl-4-[1,2,2,2-tetrafluoro-1-(trifluoromethyl)ethyl]phenyl}-N²-(1-methyl-2-methylsulphonylethyl)phthalamide, of the formula (IIc)

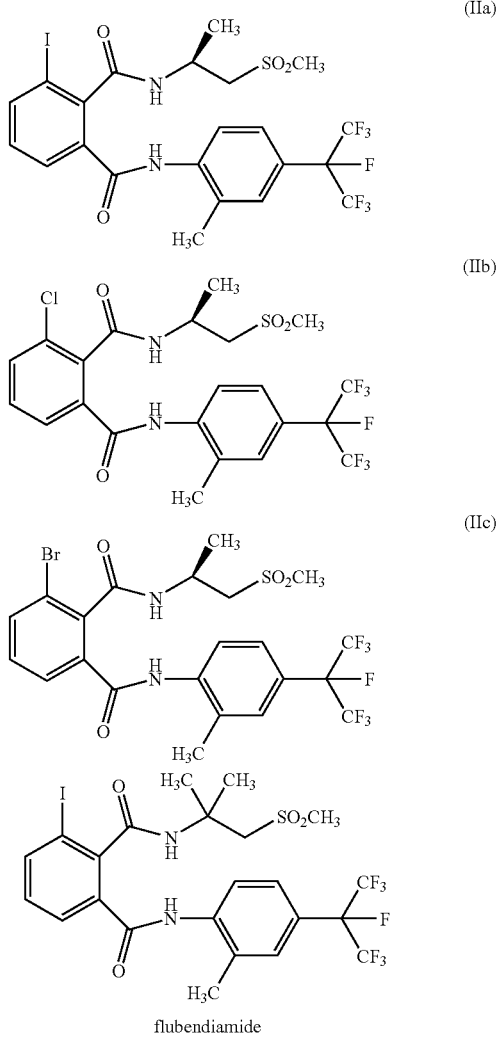

with the proviso that active substance combinations containing flubendiamide and 4-{[(6-chloropyrid-3-yl)methyl](methyl)amino}furan-2(5H)-one or 4-{[(6-chloropyrid-3-yl)methyl]-(cyclopropyl)amino}furan-2(5H)-one are excluded, are synergistically active and are suitable for controlling animal pests. Surprisingly, the insecticidal and acaricidal activity of the active substance combinations according to the invention considerably exceeds the total of the activities of the individual active substances. A true synergistic effect which cannot be predicted exists, not simply a complementation of activity.

DETAILED DESCRIPTION OF A PREFERRED EMBODIMENT

The synergistic effect of the active substance combinations according to the invention of a compound of the formula (I) and the compound from the class of the phthalic diamides widens the spectrum of action of the compound of the formula (I) and the compound from the class of the phthalic diamides primarily by reducing the dosage rate and by widening the spectrum of pests which can be controlled. Thus, a high success rate in the control of pests can always be obtained with the active substance combinations according to the invention of a compound of the formula (I) and a compound from the class of the phthalic diamides even in those cases where the individual compounds of the active substance combinations according to the invention are not sufficiently active at the low application rates used.

In addition to the above-described synergistic activity, the active substance combinations according to the invention may demonstrate further surprising advantages, including increased safety of use; reduced phytotoxicity and therefore better plant tolerance; the control of pests in their various developmental stages; better behaviour during the preparation of the insecticidal compounds, for example during grinding or mixing, during their storage or during their use; a very advantageous biocidal spectrum even at low concentrations, combined with good tolerance by warm-blooded species, fish and plants; and achieving an additional effect, for example an algicidal, anthelmintic, ovicidal, bactericidal, fungicidal, molluscicidal, nematicidal, plant-activating, rodenticidal or virucidal effect.

Furthermore, it has been found, surprisingly, that the active substance combinations according to the invention are particularly suitable for protecting seed and/or seedlings and leaves of a plant grown from the seeds from damage by pests. As a consequence, the active substance combinations according to the invention demonstrate negligible phytotoxicity when used on the plant propagation material, compatibility with soil conditions (for example as regards the locking-up of the compound in the soil), a systemic effect in the plant, no negative effect on germination, and activity during the respective pest's life cycle.

In addition to at least one compound of the formula (I), the active substance combinations according to the invention contain at least one of the phthalic diamide compounds which have been mentioned above individually. Preferably, the active substance combinations according to the invention contain precisely one compound of the formula (I) and precisely one of the phthalic diamide compounds mentioned above individually. Furthermore preferred are active substance combinations which contain a compound of the formula (I) and two of the phthalic diamide compounds mentioned above individually. Furthermore preferred are mixtures which contain two compounds of the formula (I) and one of the phthalic diamide compounds mentioned above individually.

Preferred subgroups for the compounds of the abovementioned formula (I) in the active substance combinations according to the invention with at least one of the phthalic diamide compounds mentioned above individually are listed hereinbelow, with the proviso that active substance combinations containing flubendiamides and 4-{[(6-chloropyrid-3-yl)methyl](methyl)amino}furan-2(5H)-one or 4-{[(6-chloropyrid-3-yl)methyl](cyclopropyl)amino}furan-2(5H)-one are excluded.

A preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

$R^1$ preferably represents optionally R' fluorine-substituted $C_1$-$C_5$-alkyl, $C_2$-$C_5$-alkenyl, $C_3$-$C_5$-cycloalkyl, $C_3$-$C_5$-cycloalkylalkyl or alkoxy.

A especially preferably represents the radical 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

$R^1$ especially preferably represents methyl, methoxy, ethyl, propyl, vinyl, allyl, propargyl, cyclopropyl, 2-fluoroethyl, 2,2-difluoroethyl or 2-fluorocyclopropyl.

A very especially preferably represents the radical 6-fluoropyrid-3-yl, 6-chloropyrid-3-yl, 6-bromopyrid-3-yl, 5-fluoro-6-chloropyrid-3-yl, 2-chloro-1,3-thiazol-5-yl or 5,6-dichloropyrid-3-yl.

$R^1$ very especially preferably represents methyl, cyclopropyl, methoxy, 2-fluoroethyl or 2,2-difluoroethyl.

A most preferably represents the radical 6-chloropyrid-3-yl or 5-fluoro-6-chloropyrid-3-yl.

$R^1$ most preferably represents methyl, 2-fluoroethyl or 2,2-difluoroethyl.

In a specific group of compounds of the formula (I), A represents 6-chloropyrid-3-yl

In a further specific group of compounds of the formula (I), A represents 6-bromopyrid-3-yl

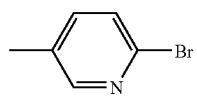

In a further specific group of compounds of the formula (I), A represents 6-chloro-1,4-pyridazin-3-yl

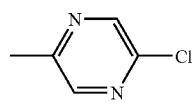

In a further specific group of compounds of the formula (I), A represents 2-chloro-1,3-thiazol-5-yl

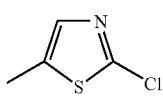

In a further specific group of compounds of the formula (I), A represents 5-fluoro-6-chloropyrid-3-yl

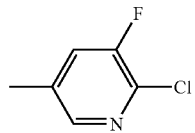

In a further specific group of compounds of the formula (I), A represents 5-fluoro-6-bromopyrid-3-yl

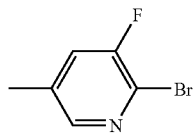

In a further specific group of compounds of the formula (I), A represents 5,6-dichloropyrid-3-yl

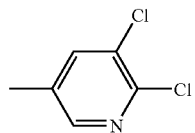

In a further specific group of compounds of the formula (I), $R^1$ represents methyl.

In a further specific group of compounds of the formula (I), $R^1$ represents ethyl.

In a further specific group of compounds of the formula (I), $R^1$ represents cyclopropyl.

In a further specific group of compounds of the formula (I), $R^1$ represents 2-fluoroethyl.

In a further specific group of compounds of the formula (I), $R^1$ represents 2,2-difluoroethyl.

The definitions of radicals, or exemplifications, which have been mentioned above in general or in preferred ranges can be combined with one another in any way, that is to say combinations between the respective preferred ranges are also possible.

Preferred in accordance with the invention are compounds of the formula (I) in which a combination of the meanings mentioned above as being preferred is present.

Particularly preferred in accordance with the invention are compounds of the formula (I) in which a combination of the meanings mentioned above as being particularly preferred is present.

Very particularly preferred in accordance with the invention are compounds of the formula (I) in which a combination of the meanings mentioned above as being very particularly preferred is present.

A preferred subgroup of the compounds of the formula (I) are those of the formula (I-a)

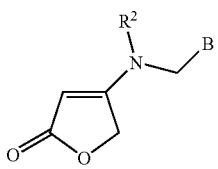

(I-a)

in which

B represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is, optionally substituted in the 2-position by chlorine or methyl, $R^2$ represents haloalkyl, haloalkenyl, halocycloalkyl or halocycloalkylalkyl.

Preferred substituents or ranges of the radicals mentioned in formula (I-a) hereinabove and hereinbelow are explained in the following text.

B preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

$R^2$ preferably represents fluorine-substituted $C_1$-$C_5$-alkyl, $C_2$-$C_5$-alkenyl, $C_3$-$C_5$-cycloalkyl or $C_3$-$C_5$-cycloalkylalkyl.

B especially preferably represents the radical 6-fluoropyrid-3-yl, 6-chloropyrid-3-yl, 6-bromopyrid-3-yl, 6-chloro-1,4-pyridazin-3-yl, 2-chloro-1,3-thiazol-5-yl.

$R^2$ particularly preferably represents 2-fluoroethyl, 2,2-difluoroethyl, 2-fluorocyclopropyl.

B very especially preferably represents the radical 6-chloropyrid-3-yl.

$R^2$ very especially preferably represents 2-fluoroethyl or 2,2-difluoroethyl.

In a specific group of compounds of the formula (I-a), B represents 6-chloropyrid-3-yl

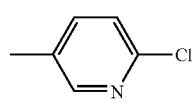

In a further specific group of compounds of the formula (I-a), B represents 6-bromopyrid-3-yl

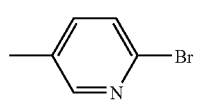

In a further specific group of compounds of the formula (I-a), B represents 6-chloro-1,4-pyridazin-3-yl

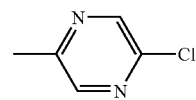

In a further specific group of compounds of the formula (I-a), $R^2$ represents 2-fluoroethyl.

In a further specific group of compounds of the formula (I-a), $R^2$ represents 2,2-difluoroethyl.

A further preferred subgroup of the compounds of the formula (I) are those of the formula (I-b)

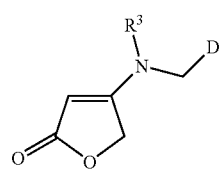

(I-b)

in which
D represents a radical

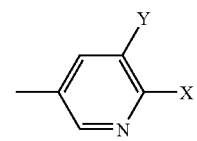

in which
X and Y have the abovementioned meanings,
$R^3$ represents hydrogen, alkyl, alkenyl, alkynyl, cycloalkyl or alkoxy.

Preferred substituents or ranges of the radicals mentioned in formula (I-b) hereinabove and hereinbelow are explained in the following text.

D preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.

$R^3$ preferably represents $C_1$-$C_4$-alkyl, $C_2$-$C_4$-alkenyl, $C_2$-$C_4$-alkynyl or $C_3$-$C_4$-cycloalkyl.

D especially preferably represents 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

$R^3$ especially preferably represents $C_1$-$C_4$-alkyl.

D very especially preferably represents 5-fluoro-6-chloropyrid-3-yl or 5-fluoro-6-bromopyrid-3-yl.

$R^3$ very especially preferably represents methyl, ethyl, propyl, vinyl, allyl, propargyl or cyclopropyl.

D most preferably represents 5-fluoro-6-chloropyrid-3-yl.
$R^3$ most preferably represents methyl or cyclopropyl.

In a further specific group of compounds of the formula (I-b), D represents 5-fluoro-6-chloropyrid-3-yl

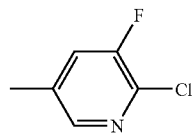

In a further specific group of compounds of the formula (I-b), D represents 5,6-dichloropyrid-3-yl

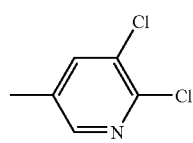

In a further specific group of compounds of the formula (I-b), D represents 5-bromo-6-chloropyrid-3-yl

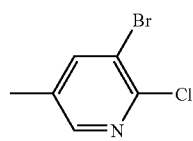

In a further specific group of compounds of the formula (I-b), D represents 5-methyl-6-chloropyrid-3-yl

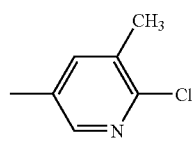

In a further specific group of compounds of the formula (I-b), D represents 5-fluoro-6-bromopyrid-3-yl

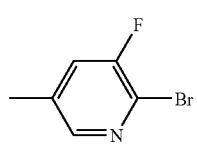

In a further specific group of compounds of the formula (I-b), D represents 5-chloro-6-bromopyrid-3-yl

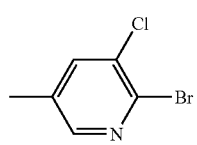

In a further specific group of compounds of the formula (I-b), D represents 5-chloro-6-iodopyrid-3-yl

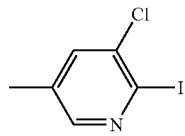

In a further specific group of compounds of the formula (I-b), $R^3$ represents methyl.

In a further specific group of compounds of the formula (I-b), $R^3$ represents ethyl.

In a further specific group of compounds of the formula (I-b), $R^3$ represents cyclopropyl.

A further preferred subgroup of the compounds of the formula (I) are those of the formula (I-c)

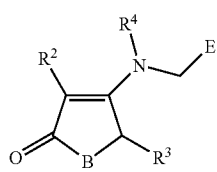

(I-c)

in which

E represents a radical

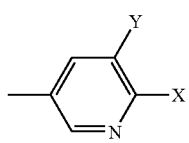

in which

X and Y have the abovementioned meanings and $R^4$ represents haloalkyl, haloalkenyl, halocycloalkyl or halocycloalkylalkyl.

Preferred substituents or ranges of the radicals mentioned in formula (I-c) hereinabove and hereinbelow are explained in the following text.

E preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.

$R^4$ preferably represents fluorine-substituted $C_1$-$C_5$-alkyl, $C_2$-$C_5$-alkenyl, $C_3$-$C_5$-cycloalkyl or $C_3$-$C_5$-cycloalkylalkyl.

E especially preferably represents 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

R⁴ especially preferably represents 2-fluoroethyl, 2,2-difluoroethyl, 2-fluorocyclopropyl.

E very especially preferably represents 5-fluoro-6-chloropyrid-3-yl.

R⁴ very especially preferably represents 2-fluoroethyl or 2,2-difluoroethyl.

In a further specific group of compounds of the formula (I-c), E represents 5-fluoro-6-chloropyrid-3-yl

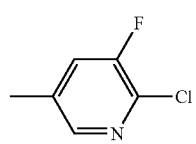

In a further specific group of compounds of the formula (I-c), E represents 5,6-dichloropyrid-3-yl

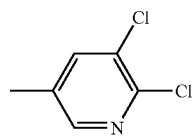

In a further specific group of compounds of the formula (I-c), E represents 5-bromo-6-chloropyrid-3-yl

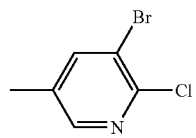

In a further specific group of compounds of the formula (I-c), E represents 5-methyl-6-chloropyrid-3-yl

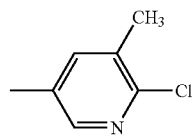

In a further specific group of compounds of the formula (I-c), E represents 5-fluoro-6-bromopyrid-3-yl

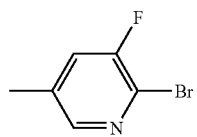

In a further specific group of compounds of the formula (I-c), E represents 5-chloro-6-bromopyrid-3-yl

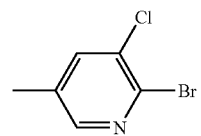

In a further specific group of compounds of the formula (I-c), E represents 5-chloro-6-iodopyrid-3-yl

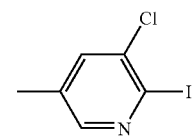

In a further specific group of compounds of the formula (I-c), R⁴ represents 2-fluoroethyl.

In a further specific group of compounds of the formula (I-c), R⁴ represents 2,2-difluoroethyl.

A preferred subgroup of the compounds of the formula (I) are those of the formula (I-d)

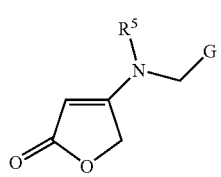

(I-d)

in which

G represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, and R⁵ represents C₁-C₄-alkyl, alkenyl, alkynyl, cycloalkyl or alkoxy, with the proviso that active substance combinations containing flubendiamide and 4-{[(6-chloropyrid-3-yl)methyl](methyl)amino}furan-2(5H)-one or 4-{[(6-chloropyrid-3-yl)methyl]-(cyclopropyl)amino}furan-2(5H)-one are excluded.

Preferred substituents or ranges of the radicals mentioned in formula (I-d) hereinabove and hereinbelow are explained in the following text.

G preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

R⁵ preferably represents C₁-C₄-alkyl, C₁-alkoxy, C₂-C₄-alkenyl, C₂-C₄-alkynyl or C₃-C₄-cycloalkyl.

G especially preferably represents the radical 6-fluoropyrid-3-yl, 6-chloropyrid-3-yl, 6-bromopyrid-3-yl, 6-chloro-1,4-pyridazin-3-yl, 2-chloro-1,3-thiazol-5-yl, $R^5$ especially preferably represents methyl, methoxy, ethyl, propyl, vinyl, allyl, propargyl or cyclopropyl.

G very especially preferably represents the radical 6-chloropyrid-3-yl.

$R^5$ very especially preferably represents methyl or cyclopropyl.

In a specific group of compounds of the formula (I-d), G represents 6-chloropyrid-3-yl

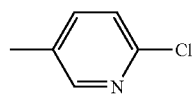

In a further specific group of compounds of the formula (I-d), G represents 6-bromopyrid-3-yl

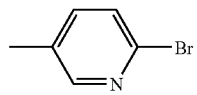

In a further specific group of compounds of the formula (I-d), G represents 6-chloro-1,4-pyridazin-3-yl

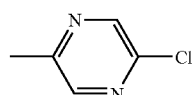

In a further specific group of compounds of the formula (I-d), G represents 2-chloro-1,3-thiazol-5-yl

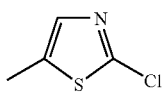

In a further specific group of compounds of the formula (I-d), G represents 6-fluoropyrid-3-yl

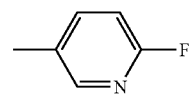

In a further specific group of compounds of the formula (I-d), G represents 6-trifluoromethylpyrid-3-yl

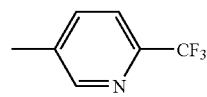

In a further specific group of compounds of the formula (I-d), G represents 6-fluoropyrid-3-yl

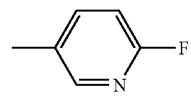

In a further specific group of compounds of the formula (I-d), $R^5$ represents methyl.

In a further specific group of compounds of the formula (I-d), $R^5$ represents cyclopropyl.

The following compounds of the general formula (I) may be mentioned individually, with the proviso that active substance combinations containing flubendiamide and 4-{[(6-chloropyrid-3-yl)methyl] (methyl)amino}furan-2(5H)-one or 4-{[(6-chloropyrid-3-yl)methyl](cyclo-propyl) amino}furan-2(5H)-one are excluded:

Compound (I-1), 4-{[(6-bromopyrid-3-yl)methyl](2-fluoroethyl)amino}furan-2(5H)-one, has the formula

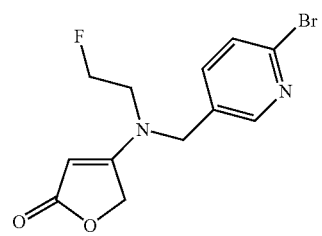 [SMILES: O=C1C=C(N(CCF)Cc2ccc(Br)nc2)CO1]

and is known from the international patent application WO 2007/115644.

Compound (I-2), 4-{[(6-fluoropyrid-3-yl)methyl](2,2-difluoroethyl)amino}furan-2(5H)-one, has the formula

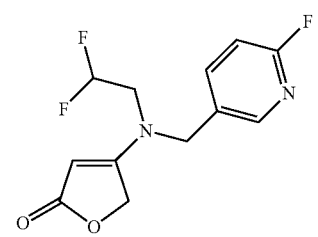 [SMILES: O=C1C=C(N(Cc2ccc(F)nc2)CC(F)F)CO1]

and is known from the international patent application WO 2007/115644.

Compound (I-3), 4-{[(2-chloro-1,3-thiazol-5-yl)methyl] (2-fluoroethyl)amino}furan-2(5H)-one, has the formula

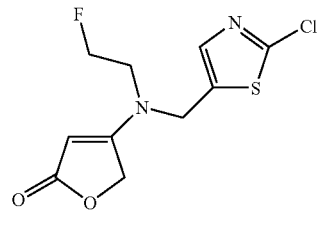 [SMILES: O=C1C=C(N(CCF)Cc2cnc(Cl)s2)CO1]

and is known from the international patent application WO 2007/115644.

Compound (I-4), 4-{[(6-chloropyrid-3-yl)methyl](2-fluoroethyl)amino}furan-2(5H)-one, has the formula

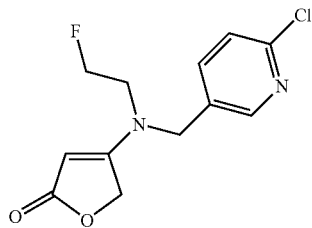 [SMILES: O=C1C=C(N(CCF)Cc2ccc(Cl)nc2)CO1]

and is known from the international patent application WO 2007/115644.

Compound (I-5), 4-{[(6-chloropyrid-3-yl)methyl](2,2-difluoroethyl)amino}furan-2(5H)-one, has the formula

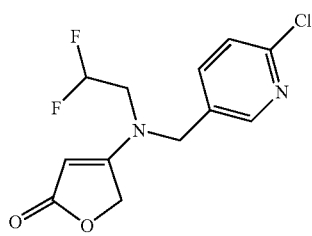 [SMILES: O=C1C=C(N(Cc2ccc(Cl)nc2)CC(F)F)CO1]

and is known from the international patent application WO 2007/115644.

Compound (I-6), 4-{[(6-chloro-5-fluoropyrid-3-yl)methyl](methyl)amino}furan-2(5H)-one, has the formula

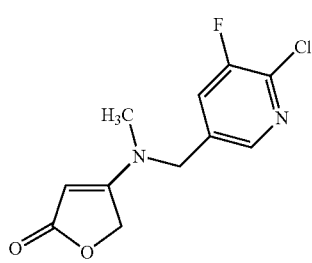 [SMILES: CN(Cc1cnc(Cl)c(F)c1)C1=CC(=O)OC1]

and is known from the international patent application WO 2007/115643.

Compound (I-7), 4-{[(5,6-dichloropyrid-3-yl)methyl](2-fluoroethyl)amino}furan-2(5H)-one, has the formula

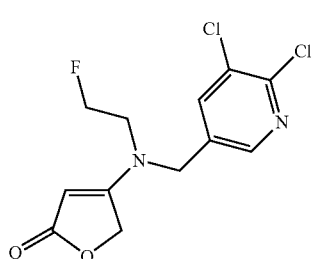

and is known from the international patent application WO 2007/115646.

Compound (I-8), 4-{[(6-chloro-5-fluoropyrid-3-yl)methyl](cyclopropyl)amino}furan-2(5H)-one, has the formula

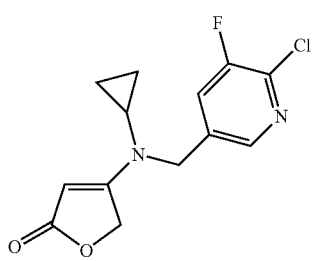 [SMILES: O=C1C=C(N(Cc2cnc(Cl)c(F)c2)C2CC2)CO1]

and is known from the international patent application WO 2007/115643.

Compound (I-9), 4-{[(6-chloropyrid-3-yl)methyl](cyclopropyl)amino}furan-2(5H)-one, has the formula

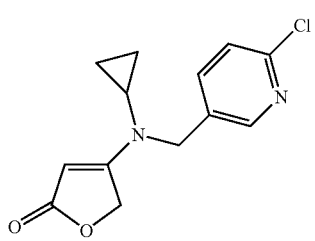 [SMILES: O=C1C=C(N(Cc2ccc(Cl)nc2)C2CC2)CO1]

and is known from EP 0 539 588.

Compound (I-10), 4-{[(6-chloropyrid-3-yl)methyl](methyl)amino}furan-2(5H)-one, has the formula

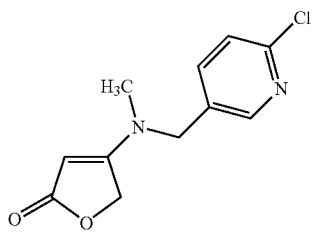 [SMILES: CN(Cc1ccc(Cl)nc1)C1=CC(=O)OC1]

and is known from EP 0 539 588.

Preferably, the active substance combinations according to the invention contain at least one of the compounds of the formula (I) which is selected from the group consisting of the compounds of the abovementioned formulae (I-a), (I-b), (1-c) or (1-d), with the proviso that active substance combinations containing flubendiamide and 4-{[(6-chloropyrid-3-yl)methyl](methyl)amino}furan-2(5H)-one or 4-{[(6-chloropyrid-3-yl)methyl](cyclopropyl)amino}furan-2(5H)-one are excluded, and one of the phthalic diamide compounds mentioned above individually.

The active substance combinations according to the invention furthermore preferably contain at least one of the compounds of the formula (I) which is selected from the group consisting of the compounds of the abovementioned formulae (I-a), (I-b) or (I-c) and one of the phthalic diamide compounds mentioned above individually.

Particularly preferably, the active substance combinations according to the invention contain at least one of the compounds of the formula (I) in which A is selected from among the radicals 6-fluoropyrid-3-yl, 6-chloropyrid-3-yl, 6-bromopyrid-3-yl, 5-fluoro-6-chloropyrid-3-yl, 2-chloro-1,3-thiazol-5-yl and 5,6-dichloropyrid-3-yl and $R^1$ is selected from among the radicals methyl, cyclopropyl, methoxy, 2-fluoroethyl or 2,2-difluoroethyl, with the proviso that active substance combinations containing flubendiamide and 4-{[(6-chloropyrid-3-yl)methyl] (methyl)amino}furan-2(5H)-one or 4-{[(6-chloropyrid-3-yl)methyl] (cyclopropyl)amino}furan-2(5H)-one are excluded, and one of the phthalic diamide compounds mentioned above individually.

Very especially preferably, the active substance combinations according to the invention contain at least one compound of the formula (I) which is selected from the group consisting of the compounds of the formulae (I-1), (I-2), (I-3), (I-4), (I-5), (I-6), (I-7), (I-8), (I-9) and (I-10) and one of the phthalic diamide compounds mentioned above individually.

This gives the combinations listed in Table 1, where each combination per se represents a very especially preferred embodiment according to the invention.

TABLE 1

Mixture containing

| Number of mixture | Compound of the formula I | | Phthalic diamide compound |
|---|---|---|---|
| 1-1 | I-1 | and | IIa |
| 1-2 | I-1 | and | IIb |
| 1-3 | I-1 | and | IIc |
| 1-4 | I-1 | and | Flubendiamide |
| 2-1 | I-2 | and | IIa |
| 2-2 | I-2 | and | IIb |
| 2-3 | I-2 | and | IIc |
| 2-4 | I-2 | and | Flubendiamide |
| 3-1 | I-3 | and | IIa |
| 3-2 | I-3 | and | IIb |
| 3-3 | I-3 | and | IIc |
| 3-4 | I-3 | and | Flubendiamide |
| 4-1 | I-4 | and | IIa |
| 4-2 | I-4 | and | IIb |
| 4-3 | I-4 | and | IIc |
| 4-4 | I-4 | and | Flubendiamide |
| 5-1 | I-5 | and | IIa |
| 5-2 | I-5 | and | IIb |
| 5-3 | I-5 | and | IIc |
| 5-4 | I-5 | and | Flubendiamide |
| 6-1 | I-6 | and | IIa |
| 6-2 | I-6 | and | IIb |
| 6-3 | I-6 | and | IIc |
| 6-4 | I-6 | and | Flubendiamide |
| 7-1 | I-7 | and | IIa |
| 7-2 | I-7 | and | IIb |
| 7-3 | I-7 | and | IIc |
| 7-4 | I-7 | and | Flubendiamide |
| 8-1 | I-8 | and | IIa |
| 8-2 | I-8 | and | IIb |
| 8-3 | I-8 | and | IIc |
| 8-4 | I-8 | and | Flubendiamide |
| 9-1 | I-9 | and | IIa |
| 9-2 | I-9 | and | IIb |
| 9-3 | I-9 | and | IIc |
| 10-1 | I-10 | and | IIa |
| 10-2 | I-10 | and | IIb |
| 10-3 | I-10 | and | IIc |

When the active substances in the active substance combinations according to the invention are present in certain weight ratios, the synergistic effect is particularly pronounced. However, the weight ratios of the active substances in the active substance combinations may be varied within a relatively large range. In general, the combinations according to the invention contain an active substance of the formula (I) and one of the active substances mentioned above individually from the class of the phthalic diamides in the following preferred and especially preferred mixing ratios:

Preferred mixing ratio: 125:1 to 1:125
Especially preferred mixing ratio: 25:1 to 1:25

The mixing ratios are based on weight ratios. The ratio is to be understood as meaning active substance of the formula (I): phthalic diamide compound. Further mixing ratios of the compound of the formula (I) to one of the phthalic diamide compounds mentioned above individually are detailed hereinbelow and are presented in the order of increasing preference of the mixing ratios: 95:1 to 1:95, 95:1 to 1:90, 95:1 to 1:85, 95:1 to 1:80, 95:1 to 1:75, 95:1 to 1:70, 95:1 to 1:65, 95:1 to 1:60, 95:1 to 1:55, 95:1 to 1:50, 95:1 to 1:45, 95:1 to 1:40, 95:1 to 1:35, 95:1 to 1:30, 95:1 to 1:25, 95:1 to 1:20, 95:1 to 1:15, 95:1 to 1:10, 95:1 to 1:5, 95:1 to 1:4, 95:1 to 1:3, 95:1 to 1:2, 90:1 to 1:90, 90:1 to 1:95, 90:1 to 1:85, 90:1 to 1:80, 90:1 to 1:75, 90:1 to 1:70, 90:1 to 1:65, 90:1 to 1:60, 90:1 to 1:55, 90:1 to 1:50, 90:1 to 1:45, 90:1 to 1:40, 90:1 to 1:35, 90:1 to 1:30, 90:1 to 1:25, 90:1 to 1:20, 90:1 to 1:15, 90:1 to 1:10, 90:1 to 1:5, 90:1 to 1:4, 90:1 to 1:3, 90:1 to 1:2, 85:1 to 1:85, 85:1 to 1:95, 85:1 to 1:90, 85:1 to 1:80, 85:1 to 1:75, 85:1 to 1:70, 85:1 to 1:65, 85:1 to 1:60, 85:1 to 1:55, 85:1 to 1:50, 85:1 to 1:45, 85:1 to 1:40, 85:1 to 1:35, 85:1 to 1:30, 85:1 to 1:25, 85:1 to 1:20, 85:1 to 1:15, 85:1 to 1:10, 85:1 to 1:5, 85:1 to 1:4, 85:1 to 1:3, 85:1 to 1:2, 80:1 to 1:80, 80:1 to 1:95, 80:1 to 1:90, 80:1 to 1:85, 80:1 to 1:75, 80:1 to 1:70, 80:1 to 1:65, 80:1 to 1:60, 80:1 to 1:55, 80:1 to 1:50, 80:1 to 1:45, 80:1 to 1:40, 80:1 to 1:35, 80:1 to 1:30, 80:1 to 1:25, 80:1 to 1:20, 80:1 to 1:15, 80:1 to 1:10, 80:1 to 1:5, 80:1 to 1:4, 80:1 to 1:3, 80:1 to 1:2, 75:1 to 1:75, 75:1 to 1:95, 75:1 to 1:90, 75:1 to 1:85, 75:1 to 1:80, 75:1 to 1:70, 75:1 to 1:65, 75:1 to 1:60, 75:1 to 1:55, 75:1 to 1:50, 75:1 to 1:45, 75:1 to 1:40, 75:1 to 1:35, 75:1 to 1:30, 75:1 to 1:25, 75:1 to 1:20, 75:1 to 1:15, 75:1 to 1:10, 75:1 to 1:5, 75:1 to 1:4, 75:1 to 1:3, 75:1 to 1:2, 70:1 to 1:70, 70:1 to 1:95, 70:1 to 1:90, 70:1 to 1:85, 70:1 to 1:80, 70:1 to 1:75, 70:1 to 1:65, 70:1 to 1:60, 70:1 to 1:55, 70:1 to 1:50, 70:1 to 1:45, 70:1 to 1:40, 70:1 to 1:35, 70:1 to 1:30, 70:1 to 1:25, 70:1 to 1:20, 70:1 to 1:15, 70:1 to 1:10, 70:1 to 1:5, 70:1 to 1:4, 70:1 to 1:3, 70:1 to 1:2, 65:1 to 1:65, 65:1 to 1:95, 65:1 to 1:90, 65:1 to 1:85, 65:1 to 1:80, 65:1 to 1:75, 65:1 to 1:70, 65:1 to 1:60, 65:1 to 1:55, 65:1 to 1:50, 65:1 to 1:45, 65:1 to 1:40, 65:1 to 1:35, 65:1 to 1:30, 65:1 to 1:25, 65:1 to 1:20, 65:1 to 1:15, 65:1 to 1:10, 65:1 to 1:5, 65:1 to 1:4, 65:1 to 1:3, 65:1 to 1:2, 60:1 to 1:60, 60:1 to 1:95, 60:1 to 1:90, 60:1 to 1:85, 60:1 to 1:80, 60:1 to 1:75, 60:1 to 1:70, 60:1 to 1:65, 60:1 to 1:55, 60:1 to 1:50, 60:1 to 1:45, 60:1 to 1:40, 60:1 to 1:35, 60:1 to 1:30, 60:1 to 1:25, 60:1 to 1:20, 60:1 to 1:15, 60:1 to 1:10, 60:1 to 1:5, 60:1 to 1:4, 60:1 to 1:3, 60:1 to 1:2, 55:1 to 1:55, 55:1 to 1:95, 55:1 to 1:90, 55:1 to 1:85, 55:1 to 1:80, 55:1 to 1:75, 55:1 to 1:70, 55:1 to 1:65, 55:1 to 1:60, 55:1 to 1:50, 55:1 to 1:45, 55:1 to 1:40, 55:1 to 1:35, 55:1 to 1:30, 55:1 to 1:25, 55:1 to 1:20, 55:1 to 1:15, 55:1 to 1:10, 55:1 to 1:5, 55:1 to 1:4, 55:1 to 1:3, 55:1 to 1:2, 50:1 to 1:95, 50:1 to 1:90, 50:1 to 1:85, 50:1 to 1:80, 50:1 to 1:75, 50:1 to 1:70, 50:1 to 1:65, 50:1 to 1:60, 50:1 to 1:55, 50:1 to 1:45, 50:1 to 1:40, 50:1 to 1:35, 50:1 to 1:30, 50:1 to 1:25, 50:1 to 1:20, 50:1 to 1:15, 50:1 to 1:10, 50:1 to 1:5, 50:1 to 1:4, 50:1 to 1:3, 50:1 to 1:2, 45:1 to 1:45, 45:1 to 1:95, 45:1 to 1:90, 45:1 to 1:85, 45:1 to 1:80, 45:1 to 1:75, 45:1 to 1:70, 45:1 to 1:65, 45:1 to 1:60, 45:1 to 1:55, 45:1 to 1:50, 45:1 to 1:40, 45:1 to 1:35, 45:1 to 1:30, 45:1 to 1:25, 45:1 to 1:20, 45:1 to 1:15, 45:1 to 1:10, 45:1 to 1:5, 45:1 to 1:4, 45:1 to 1:3, 45:1 to 1:2, 40:1 to 1:40, 40:1 to 1:95, 40:1 to 1:90, 40:1 to 1:85, 40:1 to 1:80, 40:1 to 1:75, 40:1 to 1:70, 40:1 to 1:65, 40:1 to 1:60, 40:1 to 1:55, 40:1 to 1:50, 40:1 to 1:45, 40:1 to 1:35, 40:1 to 1:30, 40:1 to 1:25, 40:1 to 1:20, 40:1 to 1:15, 40:1 to 1:10, 40:1 to 1:5, 40:1 to 1:4, 40:1 to 1:3, 40:1 to 1:2, 35:1 to 1:35, 35:1 to 1:95, 35:1 to 1:90, 35:1 to 1:85, 35:1 to 1:80, 35:1 to 1:75, 35:1 to 1:70, 35:1 to 1:65, 35:1 to 1:60, 35:1 to 1:55, 35:1 to 1:50, 35:1 to 1:45, 35:1 to 1:40, 35:1 to 1:30, 35:1 to 1:25, 35:1 to 1:20, 35:1 to 1:15, 35:1 to 1:10, 35:1 to 1:5, 35:1 to 1:4, 35:1 to 1:3, 35:1 to 1:2, 30:1 to 1:30, 30:1 to 1:95, 30:1 to 1:90, 30:1 to 1:85, 30:1 to 1:80, 30:1 to 1:75, 30:1 to 1:70, 30:1 to 1:65, 30:1 to 1:60, 30:1 to 1:55, 30:1 to 1:50, 30:1 to 1:45, 30:1 to 1:40, 30:1 to 1:35, 30:1 to 1:25, 30:1 to 1:20, 30:1 to 1:15, 30:1 to 1:10, 30:1 to 1:5, 30:1 to 1:4, 30:1 to 1:3, 30:1 to 1:2, 25:1 to 1:25, 25:1 to 1:95, 25:1 to 1:90, 25:1 to 1:85, 25:1 to 1:80, 25:1 to 1:75, 25:1 to 1:70, 25:1 to 1:65, 25:1 to 1:60, 25:1 to 1:55, 25:1 to 1:50, 25:1 to 1:45, 25:1 to 1:40, 25:1 to 1:35, 25:1 to 1:30, 25:1 to 1:20, 25:1 to 1:15, 25:1 to 1:10, 25:1 to 1:5, 25:1 to 1:4, 25:1 to 1:3, 25:1 to 1:2, 20:1 to 1:95, 20:1 to 1:90, 20:1 to 1:85, 20:1 to 1:80, 20:1 to 1:75, 20:1 to 1:70, 20:1 to 1:65, 20:1 to 1:60, 20:1 to 1:55, 20:1 to 1:50, 20:1 to 1:45, 20:1 to 1:40, 20:1 to 1:35, 20:1 to 1:30, 20:1 to 1:25, 20:1 to 1:15, 20:1 to 1:10, 20:1 to 1:5, 20:1 to 1:4, 20:1 to 1:3, 20:1 to 1:2, 15:1 to 1:15, 15:1 to 1:95, 15:1 to 1:90, 15:1 to 1:85, 15:1 to 1:80, 15:1 to 1:75, 15:1 to 1:70, 15:1 to 1:65, 15:1 to 1:60, 15:1 to 1:55, 15:1 to 1:50, 15:1 to 1:45, 15:1 to 1:40, 15:1 to 1:35, 15:1 to 1:30, 15:1 to 1:25, 15:1 to 1:20, 15:1 to 1:10, 15:1 to 1:5, 15:1 to 1:4, 15:1 to 1:3, 15:1 to 1:2, 10:1 to 1:10, 10:1 to 1:95, 10:1 to 1:90, 10:1 to 1:85, 10:1 to 1:80, 10:1 to 1:75, 10:1 to 1:70, 10:1 to 1:65, 10:1 to 1:60, 10:1 to 1:55, 10:1 to 1:50, 10:1 to 1:45, 10:1 to 1:40, 10:1 to 1:35, 10:1 to 1:30, 10:1 to 1:25, 10:1 to 1:20, 10:1 to 1:15, 10:1 to 1:5, 10:1 to 1:4, 10:1 to 1:3, 10:1 to 1:2, 5:1 to 1:5, 5:1 to 1:95, 5:1 to 1:90, 5:1 to 1:85, 5:1 to 1:80, 5:1 to 1:75, 5:1 to 1:70, 5:1 to 1:65, 5:1 to 1:60, 5:1 to 1:55, 5:1 to 1:50, 5:1 to 1:45, 5:1 to 1:40, 5:1 to 1:35, 5:1 to 1:30, 5:1 to 1:25, 5:1 to 1:20, 5:1 to 1:15, 5:1 to 1:10, 5:1 to 1:4, 5:1 to 1:3, 5:1 to 1:2, 4:1 to 1:4, 4:1 to 1:95, 4:1 to 1:90, 4:1 to 1:85, 4:1 to 1:80, 4:1 to 1:75, 4:1 to 1:70, 4:1 to 1:65, 4:1 to 1:60, 4:1 to 1:55, 4:1 to 1:50, 4:1 to 1:45, 4:1 to 1:40, 4:1 to 1:35, 4:1 to 1:30, 4:1 to 1:25, 4:1 to 1:20, 4:1 to 1:15, 4:1 to 1:10, 4:1 to 1:5, 4:1 to 1:3, 4:1 to 1:2, 3:1 to 1:3, 3:1 to 1:95, 3:1 to 1:90, 3:1 to 1:85, 3:1 to 1:80, 3:1 to 1:75, 3:1 to 1:70, 3:1 to 1:65, 3:1 to 1:60, 3:1 to 1:55, 3:1 to 1:50, 3:1 to 1:45, 3:1 to 1:40, 3:1 to 1:35, 3:1 to 1:30, 3:1 to 1:25, 3:1 to 1:20, 3:1 to 1:15, 3:1 to 1:10, 3:1 to 1:5, 3:1 to 1:4, 3:1 to 1:2, 2:1 to 1:2, 2:1 to 1:95, 2:1 to 1:90, 2:1 to 1:85, 2:1 to 1:80, 2:1 to 1:75, 2:1 to 1:70, 2:1 to 1:65, 2:1 to 1:60, 2:1 to 1:55, 2:1 to 1:50, 2:1 to 1:45, 2:1 to 1:40, 2:1 to 1:35, 2:1 to 1:30, 2:1 to 1:25, 2:1 to 1:20, 2:1 to 1:15, 2:1 to 1:10, 2:1 to 1:5, 2:1 to 1:4, 2:1 to 1:3.

The compounds of the formula (I) with at least one basic site are capable of forming for example acid addition salts, for example with strong inorganic acids such as mineral acids, for example perchloric acid, sulphuric acid, nitric acid, nitrous acid, a phosphorus acid or a hydrohalic acid, with strong organic carboxylic acids such as unsubstituted or substituted, for example halogen-substituted, $C_1$-$C_4$-alkanecarboxylic acids, for example acetic acid, saturated or unsaturated dicarboxylic acids, for example oxalic acid, malonic acid, succinic acid, maleic acid, fumaric acid and phthalic acid, hydroxycarboxylic acids, for example ascorbic acid, lactic acid, malic acid, tartaric acid and citric acid, or benzoic acid, or with organic sulphonic acids such as unsubstituted or substituted, for example halogen-substituted, $C_1$-$C_4$-alkane- or arylsulphonic acids, for example methane- or p-toluenesulphonic acid. The compounds of the formula (I) with at least one acidic group are capable of forming for example salts with bases, for example metal salts such as alkali metal or alkaline earth metal salts, for example sodium, potassium or magnesium salts, or salts with ammonia or with an organic amine such as morpholine, piperidine, pyrrolidine, a lower mono-, di- or trialkylamine, for example ethyl-, diethyl-, triethyl- or dimethylpropylamine, or a lower mono-, di- or trihydroxyalkylamine, for example mono-, di- or triethanolamine. In addition, suitable internal salts may be formed, if appropriate. Preferred within the scope of the invention are agrochemically advantageous salts. Taking into consideration the narrow relationship between the compounds of the formula (I) in free form and in the form of their salts, any reference made hereinabove and hereinbelow to the free compounds of the formula (I) or to their salts is to be understood as meaning that the corresponding salts or the free compounds of the formula (I) are also included if applicable and expedient. This also applies analogously to possible tautomers of the compounds of the formula (I) or of the compounds from the class of the phthalic diamides and to their salts.

Within the scope of the present invention, the term "active substance combination" represents various combinations of compounds of the formula (I) and active substances according to the invention from the class of the phthalic diamides, for example in the form of a single ready-mix, in a combined spray mixture consisting of separate formulations of the individual active substances, for example a tank mix, or in a combined use of the individual active substances when these are applied sequentially, for example one after the other within a suitably short period, for example a few hours or days. In accordance with a preferred embodiment, the sequence of the application of the compounds of the formula (I) and active substances according to the invention from the class of the phthalic diamides is not critical for carrying out the present invention.

When using the active substance combinations according to the invention as insecticides and acaricides, the application rates can be varied within a substantial range, depending on the type of application. In the treatment of plant parts, for example leaves, the application rate of the active substance combinations according to the invention is from 0.1 to 10 000 g/ha, preferably from 10 to 1000 g/ha, especially preferably from 50 to 300 g/ha (in the case of application by pouring or drip application, the application rate can even be reduced, especially when inert substrates such as rock wool or perlite are used); in the treatment of seed, it is from 2 to 200 g per 100 kg of seed, preferably from 3 to 150 g per 100 kg of seed, especially preferably from 2.5 to 25 g per 100 kg of seed, very especially preferably from 2.5 to 12.5 g per 100 kg of seed; in the case of soil treatment, it is from 0.1 to 10 000 g/ha, preferably from 1 to 5000 g/ha.

These application rates are only mentioned by way of example and not by way of limitation within the meaning of the invention.

The active substance combinations according to the invention can be employed for protecting plants within a certain period of time after the treatment from attack by the above-mentioned animal pests. The period of time within which protection is effected generally extends to 1 to 28 days, preferably to 1 to 14 days, especially preferably to 1 to 10 days, very especially preferably to 1 to 7 days after the treatment of the plants with the active substances, or to up to 200 days after seed treatment.

The active substance combinations according to the invention are well tolerated by plants, have favourable toxicity to warm-blooded species, show good environmental compatibility and are suitable for protecting plants and plant organs, for increasing yields, for improving the quality of the harvest crop and for controlling animal pests, in particular insects, arachnids, helminths, nematodes and molluscs, which are found in agriculture, in horticulture, in animal breeding, in forests, in gardens and leisure facilities, in the protection of stored products and materials, and in the hygiene sector. They can preferably be employed as plant protection agents. They are active against normally sensitive and resistant species and against all or individual developmental stages. The abovementioned pests include:

From the order of the Anoplura (Phthiraptera), for example *Damalinia* spp., *Haematopinus* spp., *Linognathus* spp., *Pediculus* spp., *Trichodectes* spp.

From the class of the Arachnida, for example *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example *Dreissena* spp.

From the order of the Chilopoda, for example *Geophilus* spp., *Scutigera* spp.

From the order of the Coleoptera, for example *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zea-landica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example *Onychiurus armatus.*

From the order of the Dermaptera, for example *Forficula auricularia.*

From the order of the Diplopoda, for example *Blaniulus guttulatus.*

From the order of the Diptera, for example *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

Protozoans, such as *Eimeria*, can also be controlled.

From the order of the Heteroptera, for example *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis*spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides Manus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example *Diprion* spp., *Hoplocampa* spp., *Lasius* spp., *Monomorium pharaonis, Vespa* spp.

From the order of the Isopoda, for example *Armadillidium vulgare, Oniscus asellus, Porcellio scaber.*

From the order of the Isoptera, for example *Reticulitermes* spp., *Odontotermes* spp.

From the order of the Lepidoptera, for example *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofinannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example *Ceratophyllus* spp., *Xenopsylla cheopis.*

From the order of the Symphyla, for example *Scutigerella immaculata.*

From the order of the Thysanoptera, for example *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example *Lepisma saccharina.*

The plant-parasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In certain concentrations, or at certain application rates, the active substance combinations according to the invention can, if appropriate, also be used as herbicides, safeners, growth regulators or agents for improving the plant characteristics, or as microbicides, for example as fungicides, antimycotics, bactericides, virucides (including as agents against viroids) or as agents against MLOs (mycoplasma-like organisms) and RLOs (rickettsia-like organisms).

The active substances can be converted into the customary formulations, such as solutions, emulsions, wettable powders, water- and oil-based suspensions, powders, dusts, pastes, soluble powders, soluble granules, granules for broadcasting, suspension emulsion concentrates, natural materials impregnated with active substance, synthetic materials impregnated with active substance, fertilizers and microencapsulations in polymeric materials.

These formulations are produced in a known manner, for example by mixing the active substances with extenders, that is to say liquid solvents and/or solid carriers, optionally with the use of surface-active agents, that is to say emulsifiers and/or dispersants and/or foam formers. The formulations are prepared either in suitable plants or else before or during application.

Adjuvants which may be used are those substances which are capable of imparting, to the composition itself and/or to preparations derived therefrom (for example spray mixtures, seed dressings), specific properties such as certain technical properties and/or also specific biological properties. Typical adjuvants which are suitable are: extenders, solvents and carriers.

Suitable extenders are, for example, water, polar and unpolar organic chemical fluids, for example from the classes of the aromatic and nonaromatic hydrocarbons (for example paraffins, alkylbenzenes, alkylnaphthalenes, chlorobenzenes), of the alcohols and polyols (which may optionally also be substituted, etherified and/or esterified), of the ketones (such as acetone, cyclohexanone), esters (including fats and oils) and (poly)ethers, of the unsubstituted and substituted amines, amides, lactams (such as N-alkylpyrrolidones) and lactones, of the sulphones and sulphoxides (such as dimethyl sulphoxide).

If water is used as the extender, cosolvents may also be used, for example organic solvents. Liquid solvents which are suitable are essentially: aromatics such as xylene, toluene or alkylnaphthalenes, chlorinated aromatics, or chlorinated aliphatic hydrocarbons, such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents, such as dimethyl sulphoxide, and water.

In accordance with the invention, carrier means a natural or synthetic, organic or inorganic substance which may be solid or liquid and with which the active substances are mixed or to which the active substances are bound in order to improve their use properties, in particular for application to plants or plant parts or seed. In general, the solid or liquid carrier is inert, and it should be capable of being used in agriculture.

Suitable solid or liquid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as paper, sawdust, coconut shells, maize cobs and tobacco stalks; suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: non-ionic and/or ionic substances, for example from the classes of the alcohol-POE and/or -POP ethers, acid and/or POP-POE esters, alkylaryl and/or POP-POE ethers, fatty and/or POP-POE adducts, POE- and/or POP-polyol derivatives, POE- and/or POP-sorbitan or -sugar adducts, alkyl sulphates or aryl sulphates, alkylsulphonates or arylsulphonates and alkyl phosphates or aryl phosphates, or the corresponding PO-ether adducts. Furthermore suitable are oligo- or polymers, for example those derived from vinylic monomers, from acrylic acid, from EO and/or from PO alone or in combination with, for example, (poly)alcohols or (poly)amines. It is also possible to employ lignin and its sulphonic acid derivatives, unmodified and modified celluloses, aromatic and/or aliphatic sulphonic acids, and their adducts with formaldehyde.

Tackifiers such as carboxymethylcellulose, natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanin dyestuffs, and trace nutrients such as salts of iron, manganese, boron, copper, cobalt, molybdenum and zinc.

Other possible additives are fragrances, mineral or vegetable, optionally modified, oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve the chemical and/or physical stability may also be present.

The active substance content of the use forms prepared from the commercially available formulations can vary within wide ranges. The total active substance concentration, or the active substance concentration of the individual active substances, of the use forms is in the range of from 0.00000001 to 97% by weight of active substance, preferably in the range of from 0.0000001 to 97% by weight, especially preferably in the range of from 0.000001 to 83% by weight or 0.000001 to 5% by weight and very especially preferably in the range of from 0.0001 to 1% by weight.

The active substance combinations according to the invention can be used in the present commercially available formulations and in the use forms prepared from these formulations as a mixture with further active substances such as insecticides, attractants, sterilants, bactericides, acaricides, nematicides, fungicides, growth regulators, herbicides, safeners, fertilizers or semiochemicals.

A mixture with other known active substances such as herbicides, fertilizers, growth regulators, safeners, semiochemicals, or else with agents for improving the plant properties, is also possible.

When used as insecticides, the active substance combinations according to the invention, in their commercially available formulations and in the use forms prepared from these formulations, may furthermore be present as a mixture with synergists. Synergists are compounds by which the activity of the active substances is increased without it being necessary for the synergist added to be active itself.

When used as insecticides, the active substance combinations according to the invention, in their commercially available formulations and in the use forms prepared from these formulations, may furthermore be present as a mixture with inhibitors which prevent, after application, the degradation of the active substance in the environment of the plant, on the surface of plant parts or in plant tissues.

The application is effected in a customary manner adapted to suit the use forms.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example fruits, seeds, cuttings, tubers, rhizomes, slips, seeds, bulblets, offshoots and runners.

The treatment according to the invention of the plants and plant parts with the active substance combinations is effected directly or by acting on their environment, habitat or store room by the customary treatment methods, for example by dipping, spraying, vaporizing, atomizing, scattering, painting on, injecting and, in the case of propagation material, in particular in the case of seed, furthermore by coating with one or more coats.

Plants which can be treated in accordance with the invention and which may be mentioned are the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leeks, onions), *Papilionaceae* sp. (for example peas); major crop plants such as *Gramineae* sp. (for example maize, turf, cereals such as wheat, rye, rice, barley, oats, millet/sorghum and triticale), *Asteraceae* sp. (for example sunflower), *Brassicaceae* sp. (for example white cabbage, red cabbage, broccoli, cauliflower, Brussels sprouts, pak Choi, kohlrabi, small radishes, and also oilseed rape, mustard, horseradish and cress), *Fabacae* sp. (for example beans, peanuts), *Papilionaceae* sp. (for example soybeans), *Solanaceae* sp. (for example potatoes), *Chenopodiaceae* sp. (for example sugar beet, fodder beet, swiss chard, beetroot); useful plants and ornamentals in gardens and forests; and in each case genetically modified types of these plants.

The active substance combinations according to the invention are particularly suitable for the treatment of seed. The combinations according to the invention which have been mentioned above as being preferred or especially preferred must be mentioned by preference in this context. Thus, a large proportion of the damage to crop plants which is caused by pests is already generated by infestation of the seed while the seed is stored and after the seed is introduced into the soil, and during and immediately after germination of the plants. This phase is particularly critical since the roots and shoots of the growing plant are particularly sensitive and even a small amount of damage can lead to the death of the whole plant. There is therefore in particular a great interest in protecting the seed and the germinating plant by using suitable compositions.

The control of pests by treating the seed of plants has been known for a long time and is the subject of continuous improvements. However, the treatment of seed poses a series of problems which cannot always be solved in a satisfactory manner. Thus, it is desirable to develop methods of protecting the seed and the germinating plant which dispense with the additional application of plant protection compositions after sowing or after the emergence of the plants. It is furthermore desirable to optimize the amount of the active substance employed in such a way as to provide the best possible protection for the seed and the germinating plant against attack by pests without, however, damaging the plant itself by the active substance employed. In particular, methods for the treatment of seed should also include the intrinsic insecticidal properties of transgenic plants in order to achieve an optimal protection of the seed and of the germinating plant while keeping the application rate of plant protection compositions as low as possible.

The present invention therefore particularly also relates to a method of protecting seed and germinating plants from attack by pests by treating the seed with an active substance combination according to the invention. The method according to the invention for protecting seed and germinating plants from attack by pests comprises a method in which the seed is treated simultaneously with an active substance of the formula I and one of the phthalic diamide compounds mentioned above individually. It also comprises a method in which the seed is treated at different times with an active substance of the formula I and one of the phthalic diamide compounds mentioned above individually. The invention likewise relates to the use of the active substance combinations according to the invention for the treatment of seed for protecting the seed and the plant which it gives rise to from pests. The invention furthermore relates to seed which has been treated with an active substance combination according to the invention as a protection from pests. The invention also relates to seed which has been treated simultaneously with an active substance of the formula I and one of the phthalic diamide compounds mentioned above individually. The invention furthermore relates to seed which has been treated at different times with an active substance of the formula I and one of the phthalic diamide compounds mentioned above individually. In the case of seed which has been treated at different times with an active substance of the formula I and one of the phthalic diamide compounds mentioned above individually, the individual active substances of the composition according to the invention may be present on the seed in different layers. In this context, the layers which contain an active substance of the formula I and one of the phthalic diamide compounds mentioned above individually may, if appropriate, be separated by an intermediate layer. The invention also relates to seed where an active substance of the formula I and one of the phthalic diamide compounds mentioned above individually are applied as component of a coat or as further layer(s) in addition to a coat.

One of the advantages of the present invention is that, owing to the particular systemic properties of some of the active substance combinations according to the invention, the treatment of the seed with these active substance combinations does not only protect the seed itself from pests, but also the plants which it gives rise to, after they have emerged. In this manner, the immediate treatment of the crop at the point in time of sowing or shortly thereafter can be dispensed with.

A further advantage is the synergistic increase of the insecticidal activity of the active substance combinations according to the invention in comparison with the individual insecticidal active substance, which exceeds the activity to be expected when the two active substances are employed individually. Another advantage is the synergistic increase of the fungicidal activity of the active substance combinations according to the invention in comparison with the individual fungicidal active substance, which exceeds the activity to be expected when the active substance is employed individually. This makes possible an optimization of the amount of the active substances employed.

The fact that the active substance combinations according to the invention can also be employed in particular in transgenic seed, where the plants which this seed gives rise to are capable of expressing a protein directed against pests, can be seen as another advantage. As the result of the treatment of such seed with the active substance combinations according to the invention, certain pests can already be controlled by the expression of the, for example, insecticidal protein, and can additionally be safeguarded from damage by the active substance combinations according to the invention.

The active substance combinations according to the invention are suitable for the protection of seed of any plant variety as already mentioned above which is employed in agriculture, in the greenhouse, in forests or in horticulture. In particular, this takes the form of seed of maize, peanut, canola, oilseed rape, poppy, soya, cotton, beet (for example sugar beet and fodder beet), rice, sorghum and millet, wheat, barley, oats, rye, sunflower, tobacco, potatoes or vegetables (for example tomatoes, brassicas). The active substance combinations according to the invention are also suitable for the treatment of the seed of fruit plants and vegetables as already mentioned above. Particularly important is the treatment of the seed of maize, soya, cotton, wheat and canola or oilseed rape.

As already mentioned above, the treatment of transgenic seed with an active substance combination according to the invention is also particularly important. This may take the form of seed of plants which, as a rule, comprise at least one heterologous gene which controls the expression of a polypeptide with, in particular, insecticidal properties. The heterologous genes in transgenic seed can be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene from *Bacillus* sp. and whose gene product shows activity against the European corn borer and/or the corn rootworm. Especially preferably, this takes the form of a heterologous gene from *Bacillus thuringiensis*.

Within the scope of the present invention, the active substance combination according to the invention is applied to the seed either alone or in the form of a suitable formulation. The seed is preferably treated in a state in which it is sufficiently stable to avoid damage during the treatment. In general, treatment of the seed can be effected at any point in time between harvest and sowing. Usually, seed is used which has been separated from the plant and freed from cobs, hulls, stems, coats, hair or pulp.

When treating seed, care must be taken generally that the amount of the active substance combination according to the invention and/or further additives which is/are applied to the seed is chosen in such a way that the germination of the seed is not adversely affected, or the plant which the seed gives rise to is not damaged. This is in particular the case for active substances which may have phytotoxic effects at certain application rates.

The compositions according to the invention can be applied directly, which means without comprising further components and without having been diluted. As a rule, it is preferable to apply the compositions to the seed in the form of a suitable formulation. Suitable formulations and methods for the treatment of seed are known to the skilled worker and are described, for example, in the following documents: U.S. Pat. Nos. 4,272,417 A, 4,245,432 A, 4,808,430 A, 5,876,739 A, US 2003/0176428 A1, WO 2002/080675 A1, WO 2002/028186 A2.

The active substances which can be used according to the invention can be converted into the customary seed-dressing product formulations such as solutions, emulsions, suspensions, powders, foams, slurries and other coating compositions for seed, and ULV formulations.

These formulations are prepared in the known manner by mixing the active substances with customary additives such as, for example, customary extenders and also solvents or diluents, colorants, wetters, dispersants, emulsifiers, antifoams, preservatives, secondary thickeners, adhesives, gibberellins, and also water.

Colorants which may be present in the seed-dressing product formulations which can be used according to the invention are all colorants which are customary for such purposes. Both pigments, which are sparingly soluble in water, and dyes, which are soluble in water, may be used. Examples of colorants which may be mentioned are those known by the names Rhodamin B, C.I. Pigment Red 112 and C.I. Solvent Red 1.

Wetters which may be present in the seed-dressing product formulations which can be used according to the invention are all substances which are conventionally used for the formulation of agrochemical active substances and for promoting wetting. Alkylnaphthalenesulphonates, such as diisopropyl- or diisobutylnaphthalenesulphonates, can preferably be used.

Suitable dispersants and/or emulsifiers which may be present in the seed-dressing product formulations which can be used in accordance with the invention are all non-ionic, anionic and cationic dispersants which are conventionally used for the formulation of agrochemical active substances. Non-ionic or anionic dispersants or mixtures of non-ionic or anionic dispersants can preferably be used. Suitable non-ionic dispersants which may be mentioned are, in particular, ethylene oxide/propylene oxide block polymers, alkylphenol polyglycol ethers and tristryrylphenol polyglycol ethers, and their phosphated or sulphated derivatives. Suitable anionic dispersants are, in particular, lignosulphonates, polyacrylic acid salts and arylsulphonate/formaldehyde condensates.

Antifoams which may be present in the seed-dressing product formulations which can be used according to the invention are all foam-suppressing substances conventionally used for the formulation of agrochemical active substances. Silicone antifoams and magnesium stearate can preferably be used.

Preservatives which may be present in the seed-dressing product formulations which can be used according to the invention are all substances which can be employed in agrochemical compositions for such purposes. Examples which may be mentioned are dichlorophene and benzyl alcohol hemiformal.

Secondary thickeners which may be present in the seed-dressing product formulations which can be used according to the invention are all substances which can be employed in agrochemical compositions for such purposes. Cellulose derivatives, acrylic acid derivatives, xanthan, modified clays and highly disperse silica are preferably suitable.

Adhesives which may be present in the seed-dressing product formulations which can be used according to the invention are all customary binders which can be employed in seed-dressing products. Polyvinylpyrrolidone, polyvinyl acetate, polyvinyl alcohol and tylose may be mentioned by preference.

Gibberellins which may be present in the seed-dressing product formulations which can be used according to the invention are preferably the gibberellins A1, A3 (=gibberellic acid), A4 and A7, with gibberellic acid being particularly preferably used. The gibberellins are known (cf. R. Wegler "Chemie der Pflanzenschutz- and Schadlingsbekampfungsmittel" [Chemistry of Plant Protectants and Pesticides], Vol. 2, Springer Verlag, 1970, pp. 401-412).

The seed-dressing product formulations which can be used in accordance with the invention can be employed either directly or after previous dilution with water for the treatment of a wide range of seeds, including the seed of transgenic plants. In this context, additional synergistic effects may also occur as a consequence of the interaction with the substances formed by expression.

Suitable apparatuses which can be employed for treating seed with the seed-dressing product formulations which can be used in accordance with the invention, or with the preparations prepared therefrom by addition of water, are all mixing apparatuses which can usually be employed for dressing seed. Specifically, a seed-dressing procedure is followed in which the seed is placed in a mixer, the amount of seed-dressing product formulation desired in each case is added, either as such or after previously diluting it with water, and the contents of the mixer are mixed until the formulation has been distributed uniformly on the seed. If appropriate, this is followed by a drying process.

As already mentioned above, all plants and their parts can be treated in accordance with the invention. In a preferred embodiment, plant species and plant varieties which are found in the wild or which are obtained by traditional biological breeding methods, such as hybridization or protoplast fusion, and parts of the former are treated. In a further preferred embodiment, transgenic plants and plant varieties which have been obtained by recombinant methods, such as, for example, antisense or cosuppression technology, RNA interference—RNAi—technology, if appropriate in combination with traditional methods (genetically modified organisms) and their parts are treated. The terms "parts" or "parts of plants" or "plant parts" have been explained above.

It is especially preferred to treat in accordance with the invention plants of the plant varieties which are in each case commercially available or in use. Plant varieties are understood as meaning plants with novel traits which have been generated either by conventional breeding, by mutagenesis or by recombinant DNA techniques. They may take the form of varieties, biotypes and genotypes.

Depending on the plant species or plant varieties, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage ability and/or processability of the harvested products which exceed the effects which were actually to be expected are possible.

The preferred transgenic plants or plant varieties (i.e. those obtained by genetic engineering) which are to be treated according to the invention include all plants which, as a result of the recombinant modification, received genetic material which imparted particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage ability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidal active substances. Examples of transgenic plants which may be mentioned are the important crop plants, such as cereals (wheat, rice), maize, soybeans, potatoes, sugar beet, tomatoes, peas and other types of vegetables, cotton, tobacco, oilseed rape and also fruit plants (with the fruits apples, pears, citrus fruits and grapes), and particular emphasis is given to maize, soybeans, potatoes, cotton, tobacco and oilseed rape. Traits that are emphasized in particular are increased defence of the plants against insects, arachnids, nematodes, slugs and snails as the result of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also especially emphasized are the increased defence of plants against fungi, bacteria and viruses as the result of systemic acquired resistance (SAR), systemin, phytoalexins, elicitors and resistance genes, and suitably expressed proteins and toxins. Traits that are furthermore particularly emphasized are the increased tolerance of the plants to certain herbicidal active substances, for example imidazolinones, sulphonylureas, glyphosate or phosphinothricin (for example the "PAT" gene). The genes which impart the desired traits in question can also be present in combinations with one another in the transgenic plants. Examples of "Bt plants" which may be mentioned are maize varieties, cotton varieties, soybeans varieties and potato varieties which are sold under the trade names YIELD GARD® (for example maize, cotton, soybeans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soybeans varieties which are sold under the trade names Roundup Ready® (tolerance to glyphosates, for example maize, cotton, soybeans), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant varieties which are developed in the future, or will be commercially available in the future, and which have these genetic traits or genetic traits yet to be developed.

The plants listed can be treated in a particularly advantageous manner with the active substance combinations according to the invention. The preferred ranges stated above for the active substance combinations also apply to the treatment of these plants. Particular emphasis is given to the treatment of plants with the active substance combinations specifically mentioned in the present text.

The active substance combinations according to the invention are not only active against plant pests, hygiene pests and stored-product pests, but also, in the sector of veterinary medicine, against animal parasites (ecto- and endoparasites) such as hard ticks, soft ticks, scab mites, harvest mites, flies (stinging and licking), parasitic fly larvae, lice, hair lice, bird lice and flees. These parasites include:

From the order of the Anoplurida, for example *Haematopinus* spp., *Linognathus* spp., *Pediculus* spp., *Phtirus* spp., *Solenopotes* spp.

From the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example *Pulex* spp., *Ctenocephalides* spp., *Xenopsylla* spp., *Ceratophyllus* spp.

From the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp.

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active substance combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honeybees, other domestic animals such as, for example, dogs, cats, cage birds, aquarium fish and what are known as experimental animals such as, for example, hamsters, guinea pigs, rats and mice. By controlling these arthropods, it is intended to reduce deaths and performance reductions (in the case of meat, milk, wool, hides, eggs, honey and the like), so that more economical and simpler animal keeping is made possible by the use of the active substance combinations according to the invention.

In the veterinary sector and in animal keeping, the active substance combinations according to the invention are applied in the known manner by enteral administration in the form of, for example, tablets, capsules, drinks, drenches, granules, pastes, boluses, the feed-through method, suppositories, by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-substance-comprising shaped articles such as collars, ear tags, tail tags, limb bands, halters, marking devices and the like.

When used for livestock, poultry, domestic animals and the like, the active substance combinations can be applied as formulations (for example powders, emulsions, flowables) which comprise the active substances in an amount of from 1 to 80% by weight, either directly or after 100- to 10 000-fold dilution, or else as a chemical bath.

Furthermore, it has been found that the active substance combinations according to the invention have a potent insecticidal activity against insects which destroy industrial materials.

The following insects may be mentioned by way of example and by preference, but not by limitation:

Beetles such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenoptera such as *Sirex juvencus, Urocerus gigas, Urocerus gigas taignus, Urocerus augur.*

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails such as *Lepisma saccharina.*

Industrial materials are understood as meaning, in the present context, non-live materials such as, preferably, polymers, adhesives, glues, paper and board, leather, wood, derived timber products and paints.

If appropriate, the ready-to-use compositions may additionally comprise further insecticides and, if appropriate, additionally one or more fungicides.

As regards potential additional components in mixtures, reference may be made to the abovementioned insecticides and fungicides.

The active substance combinations according to the invention can also be employed for protecting against growth on objects, in particular ships' hulls, sieves, nets, buildings, moorings and signal systems which come into contact with salt water or brackish water.

Furthermore, the active substance combinations according to the invention, alone or in combinations with other active substances, may be employed as antifouling agents.

The active substance combinations are also suitable for controlling animal pests in the protection of domestic premises, in the field of hygiene and of stored products, in particular insects, arachnids and mites which are found in enclosed spaces such as, for example, dwellings, factory halls, offices, drivers' cabins and the like. To control these pests they can be used in insecticidal products for domestic premises, either alone or in combination with other active substances and auxiliaries. They are active against sensitive and resistant species and against all developmental stages. These pests include:

From the order of the Scorpionidea, for example *Buthus occitanus.*

From the order of the Acarina, for example *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example *Aviculariidae, Araneidae.*

From the order of the Opiliones, for example *Pseudoscorpiones chelifer, Pseudoscorpiones cheiridium, Opiliones phalangium.*

From the order of the Isopoda, for example *Oniscus asellus, Porcellio scaber.*

From the order of the Diplopoda, for example *Blaniulus guttulatus, Polydesmus* spp.

From the order of the Chilopoda, for example *Geophilus* spp.

From the order of the Zygentoma, for example *Ctenolepisma* spp., *Lepisma saccharina, Lepismodes inquilinus.*

From the order of the Blattaria, for example *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example *Acheta domesticus.*

From the order of the Dermaptera, for example *Forficula auricularia.*

From the order of the Isoptera, for example *Kalotermes* spp., *Reticulitermes* spp.

From the order of the Psocoptera, for example *Lepinatus* spp., *Liposcelis* spp.

From the order of the Coleoptera, for example *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example *Achroia grisella, Galleria mellonella, Plodia interpunctella, Tinea cloacella, Tinea pellionella, Tineola bisselliella.*

From the order of the Siphonaptera, for example *Ctenocephalides canis, Ctenocephalides felis, Pulex irritans, Tunga penetrans, Xenopsylla cheopis.*

From the order of the Hymenoptera, for example *Camponotus herculeanus, Lasius fuliginosus, Lasius niger, Lasius umbratus, Monomorium pharaonis, Paravespula* spp., *Tetramorium caespitum.*

From the order of the Anoplura, for example *Pediculus humanus capitis, Pediculus humanus corporis, Pemphigus* spp., *Phylloera vastatrix, Phthirus pubis.*

From the order of the Heteroptera, for example *Cimex hemipterus, Cimex lectularius, Rhodinus prolixus, Triatoma infestans.*

The application in the field of the domestic insecticides is carried out alone or in combination with other suitable active substances such as phosphoric esters, carbamates, pyrethroids, neo-nicotinoids, growth regulators or active substances from other known classes of insecticides.

The application is carried out in aerosols, unpressurized sprays, for example pump sprays and atomizer sprays, automatic misting devices, foggers, foams, gels, vaporizer products with vaporizer platelets made of cellulose or polymer, liquid vaporizers, gel and membrane vaporizers, propeller-driven vaporizers, vaporization systems which do not consume energy (passive vaporization systems), moth papers, moth sachets and moth gels in the form of granules or dusts, in baits for scattering or bait stations.

The good insecticidal and acaricidal activity of the active substance combinations according to the invention can be seen from the examples which follow. While the individual active substances show weaknesses in their activity, the combinations demonstrate an activity which exceeds a simple sum of activities.

A synergistic effect in insecticides and acaricides is always present when the activity of the active substance combinations exceeds the total of the activities of the active substances applied individually.

The activity to be expected for a given combination of two active substances can be calculated, as described by S. R. Colby, Weeds 15 (1967), 20-22, as follows:

If

X means the degree of destruction expressed in % of the untreated control when using active substance A at an application rate of m g/ha or at a concentration of m ppm, Y means the degree of destruction expressed in % of the untreated control when using active substance B at an application rate of n g/ha or at a concentration of n ppm, and E means the degree of destruction expressed in % of the untreated control when employing active substances A and B at application rates of m and n g/ha or at a concentration of m and n ppm, then $$E = X + Y - \frac{X \cdot Y}{100}$$

If the actual insecticidal or acaricidal degree of destruction is greater than calculated, the combination is superadditive regarding its destruction, i.e. a synergistic effect is present. In this case, the degree of destruction which is actually observed must exceed the value calculated on the basis of the above formula for the expected degree of destruction (E).

EXAMPLE A1

*Myzus persicae* Test

| Solvent: | 78 parts by weight of acetone |
| | 1.5 parts by weight of dimethylformamide |
| Emulsifier: | 0.5 parts by weight of alkylaryl polyglycol ether |

To prepare a suitable preparation of active substance, 1 part by weight of active substance is mixed with the stated amounts of solvent and emulsifier, and the concentrate is diluted to the desired concentration with emulsifier-containing water.

Cabbage leaves (*Brassica oleracea*) which are severely infested with the green peach aphid (*Myzus persicae*) are treated by spraying with the active substance preparation at the desired concentration.

After the desired period of time, the destruction is determined in %. Here, 100% means that all the aphids have been destroyed; 0% means that no aphids have been destroyed. The destruction rates which have been determined are entered in the above Colby formula.

In this test, a synergistically increased activity in comparison with the active substances applied individually is demonstrated for example by the following active substance combinations according to the invention:

TABLE A1

*Myzus persicae* test

| Active substance | Concentration in g/ha | Destruction in % after 1 day | |
|---|---|---|---|
| Compound I-4 | 4 | 30 | |
| Compound I-6 | 0.16 | 30 | |
| Compound IIb | 0.8 | 0 | |
| Flubendiamide | 0.16 | 0 | |
| | | found* | calc.** |
| Compound I-4 + Compound IIb (5:1) | 4 + 0.8 | 50 | 30 |
| | | found* | calc.** |
| Compound I-6 + Flubendiamide (1:1) | 0.16 + 0.16 | 70 | 30 |

*found = found activity;
**calc. = activity calculated with the Colby formula

EXAMPLE A2

*Myzus persicae* Test

| Solvent: | 7 parts by weight of dimethylformamide |
| Emulsifier: | 2 parts by weight of alkylaryl polyglycol ether |

To prepare a suitable preparation of active substance, 1 part by weight of active substance is mixed with the stated amounts of solvent and emulsifier, and the concentrate is diluted to the desired concentration with emulsifier-containing water.

Cabbage leaves (*Brassica oleracea*) which are severely infested with the green peach aphid (*Myzus persicae*) are treated by dipping into the active substance preparation of the desired concentration.

After the desired period of time, the destruction is determined in %. Here, 100% means that all the aphids have been destroyed; 0% means that no aphids have been destroyed. The destruction rates which have been determined are entered in the above Colby formula.

In this test, a synergistically increased activity in comparison with the active substances applied individually is demonstrated by the following active substance combination according to the invention:

TABLE A2

*Myzus persicae* test

| Active substance | Concentration in ppm | Destruction in % after 1 day | |
|---|---|---|---|
| Compound I-10 | 0.8 | 45 | |
| Compound IIb | 100 | 10 | |
| Compound I-10 + Compound IIb | | found* | calc.** |
| (1:125) | 0.8 + 100 | 75 | 50.5 |

*found = found activity;
**calc. = activity calculated with the Colby formula

EXAMPLE B

Phaedon Cochleariae Larvae Test

| Solvent: | 78 parts by weight of acetone |
| --- | --- |
|  | 1.5 parts by weight of dimethylformamide |
| Emulsifier: | 0.5 parts by weight of alkylaryl polyglycol ether |

To prepare a suitable preparation of active substance, 1 part by weight of active substance is mixed with the stated amounts of solvent and emulsifier, and the concentrate is diluted to the desired concentration with emulsifier-containing water.

Cabbage leaves (Brassica oleracea) are treated by spraying with the active substance preparation at the desired concentration and populated with mustard beetle larvae (Phaedon cochleariae) while the leaves are moist.

After the desired period of time, the destruction is determined in %. Here, 100% means that all the beetle larvae have been destroyed; 0% means that no beetle larvae have been destroyed. The destruction rates which have been determined are entered in the above Colby formula.

In this test, a synergistically increased activity in comparison with the active substances applied individually is demonstrated by the following active substance combinations according to the invention:

TABLE B

Phaedon cochleariae larvae test

| Active substance | Concentration in g/ha | Destruction in % after 2 days | |
| --- | --- | --- | --- |
| Compound I-4 | 100 | 0 | |
| Compound I-6 | 100 | 0 | |
| Flubendiamide | 100 | 17 | |
|  |  | found* | calc.** |
| Compound I-4 + Flubendiamide (1:1) | 100 + 100 | 33 | 17 |
|  |  | found* | calc.** |
| Compound I-6 + Flubendiamide (1:1) | 100 + 100 | 33 | 17 |

*found = found activity;
**calc. = activity calculated with the Colby formula

EXAMPLE C

Spodoptera frugiperda Larvae Test

| Solvent: | 78 parts by weight of acetone |
| --- | --- |
|  | 1.5 parts by weight of dimethylformamide |
| Emulsifier: | 0.5 parts by weight of alkylaryl polyglycol ether |

To prepare a suitable preparation of active substance, 1 part by weight of active substance is mixed with the stated amounts of solvent and emulsifier, and the concentrate is diluted to the desired concentration with emulsifier-containing water.

Cabbage leaves (Brassica oleracea) are treated by spraying with the active substance preparation at the desired concentration and populated with army worm larvae (Spodoptera frugiperda) while the leaves are moist.

After the desired period of time, the destruction is determined in %. Here, 100% means that all the caterpillars have been destroyed; 0% means that no caterpillars have been destroyed. The destruction rates which have been determined are entered in the above Colby formula.

In this test, a synergistically increased activity in comparison with the active substances applied individually is demonstrated by the following active substance combinations according to the invention:

TABLE C

Spodoptera frugiperda larvae test

| Active substance | Concentration in g/ha | Destruction in % after 6 days | |
| --- | --- | --- | --- |
| Compound I-4 | 4 | 0 | |
| Compound I-5 | 0.8 | 0 | |
| Compound I-6 | 4 | 0 | |
| Compound IIb | 0.8 | 67 | |
|  | 0.16 | 0 | |
| Flubendiamide | 4 | 67 | |
|  | 0.8 | 33 | |
|  |  | found* | calc.** |
| Compound I-4 + Compound IIb (5:1) | 4 + 0.8 | 100 | 67 |
|  |  | found* | calc.** |
| Compound I-5 + Compound IIb (5:1) | 0.8 + 0.16 | 33 | 0 |
|  |  | found* | calc.** |
| Compound I-6 + Flubendiamide (1:1) | 4 + 4 | 83 | 67 |
|  |  | found* | calc.** |
| Compound I-5 + Flubendiamide (1:1) | 0.8 + 0.8 | 67 | 33 |
|  |  | found* | calc.** |
| Compound I-6 + Flubendiamide (1:1) | 4 + 4 | 100 | 67 |

*found = found activity;
**calc. = activity calculated with the Colby formula

The invention claimed is:

1. An active substance combination comprising at least one compound selected from the group consisting of compound (I-1), 4-{[(6-bromopyrid-3-yl)methyl](2-fluoroethyl)amino}furan-2(5H)-one

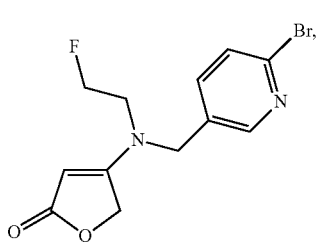

(I-1)

compound (I-2), 4-{[(6-fluoropyrid-3-yl)methyl](2,2-difluoroethyl)amino}furan-2(5H)-one

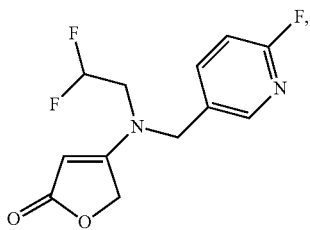

compound (I-3), 4-{[(2-chloro-1,3-thiazol-5-yl)methyl](2-fluoroethyl)amino}furan-2(5H)-one

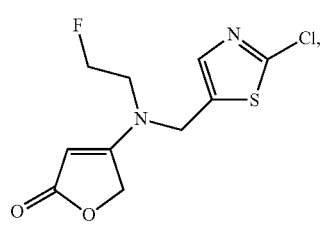

compound (I-4), 4-{[(6-chloropyrid-3-yl)methyl](2-fluoroethyl)amino}furan-2(5H)-one

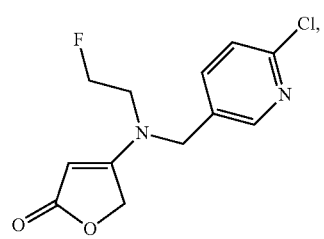

compound (I-5), 4-{[(6-chloropyrid-3-yl)methyl](2,2-difluoroethyl)amino}furan-2(5H)-one

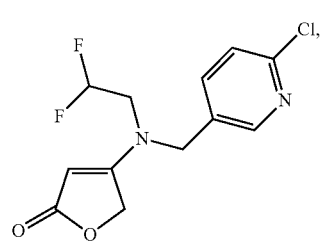

compound (I-6), 4-{[(6-chloro-5-fluoropyrid-3-yl)methyl](methyl)amino}furan-2(5H)-one

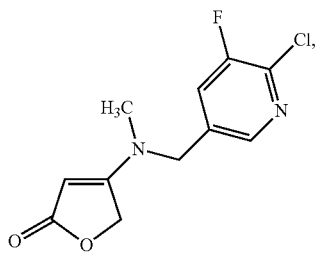

compound (I-7), 4-{[(5,6-dichloropyrid-3-yl)methyl](2-fluoroethyl)amino}furan-2(5H)-one

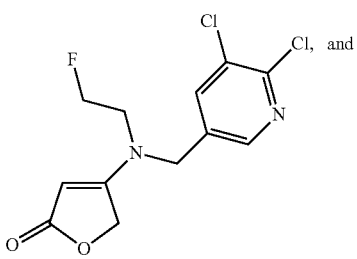

compound (I-8), 4-{[(6-chloro-5-fluoropyrid-3-yl)methyl](cyclopropyl)amino}furan-2(5H)-one

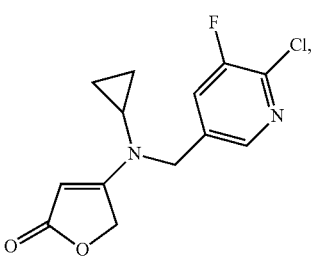

and at least one phthalic diamide compound selected from the group consisting of flubendiamide, (S)-3-iodo-$N^1$-{2-methyl-4-[1,2,2,2-tetrafluoro-1-(trifluoromethyl)ethyl]-phenyl}-$N^2$-(1-methyl-2-methylsulphonylethyl)phthalamide,(S)-3-chloro-$N^1$-{2-methyl-4-[1,2,2,2-tetrafluoro-1-(trifluoromethyl)ethyl]phenyl}-$N^2$-(1-methyl-2-methylsulphonyl-ethyl)phthalamide and (S)-3-bromo-$N^1$-{2-methyl-4-[1,2,2,2-tetrafluoro-1-(trifluoromethyl)ethyl]phenyl}-$N^2$-(1-methyl-2-methylsulphonylethyl)phthalamide.

2. Method of controlling pests of animals, comprising allowing an active substance combination to act on pests of animals and/or an environment thereof and/or on seed,
wherein the active substance combination comprises at least one compound selected from the group consisting of compound (I-1), 4-{[(6-bromopyrid-3-yl)methyl](2-fluoroethyl)amino}furan-2(5H)-one

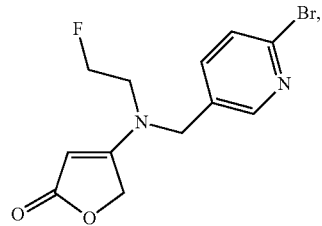
(I-1)

compound (I-2), 4-{[(6-fluoropyrid-3-yl)methyl](2,2-difluoroethyl)amino}furan-2(5H)-one

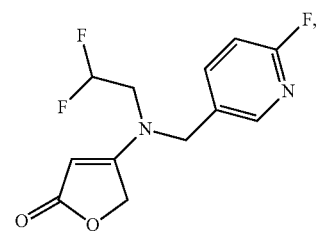
(I-2)

compound (I-3), 4-{[(2-chloro-1,3-thiazol-5-yl)methyl](2-fluoroethyl)amino}furan-2(5H)-one

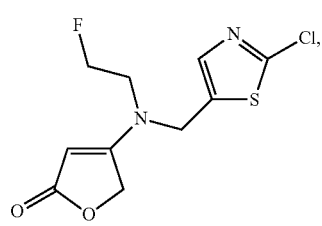
(I-3)

compound (I-4), 4-{[(6-chloropyrid-3-yl)methyl](2-fluoroethyl)amino}furan-2(5H)-one

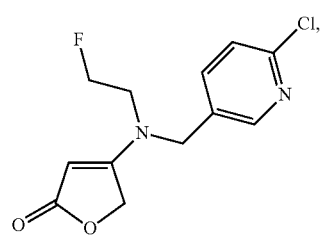
(I-4)

compound (I-5), 4-{[(6-chloropyrid-3-yl)methyl](2,2-difluoroethyl)amino}furan-2(5H)-one

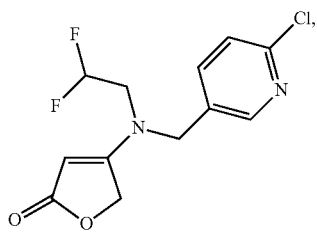
(I-5)

compound (I-6), 4-{[(6-chloro-5-fluoropyrid-3-yl)methyl](methyl)amino}furan-2(5H)-one

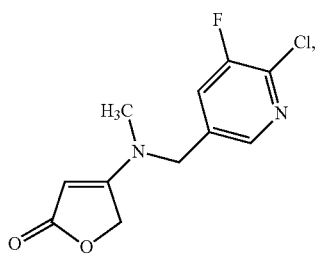
(I-6)

compound (I-7), 4-{[(5,6-dichloropyrid-3-yl)methyl](2-fluoroethyl)amino}furan-2(5H)-one

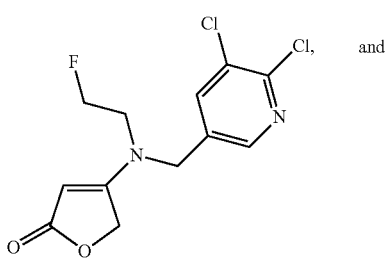
(I-7)

compound (I-8), 4-{[(6-chloro-5-fluoropyrid-3-yl)methyl](cyclopropyl)amino}furan-2(5H)-one

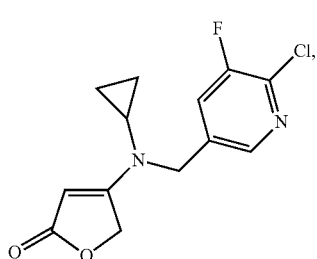
(I-8)

and at least one phthalic diamide compound selected from the group consisting of flubendiamide, (S)-3-iodo-$N^1$-{2-methyl-4-[1,2,2,2-tetrafluoro-1-(trifluoromethyl)ethyl]-phenyl}-$N^2$-(1-methyl-2-methylsulphonylethyl)phthalamide,(S)-3-chloro-$N^1$-{2-methyl-4-[1,2,2,2-tetrafluoro-1-(trifluoromethyl)ethyl]phenyl}-$N^2$-(1- methyl-2-methylsulphonyl-ethyl)phthalamide and (S)-3-bromo-N¹-{2-methyl-4-[1,2,2,2-tetrafluoro-1-(trifluoromethyl)ethyl]phenyl}-N²-(1-methyl-2-methylsulphonylethyl)phthalamide.

3. Method according to claim 2, wherein the at least one compound and said at least one phthalic diamide compound are simultaneously allowed to act on seed.

4. Method according to claim 2, wherein the at least one compound and said at least one phthalic diamide compound are allowed to act on seed at different times.

5. Method for the preparation of an insecticidal and/or acaricidal compositions, comprising mixing an active substance combination with an extender and/or surface-active substance,
wherein the active substance combination comprises at least one compound selected from the group consisting of compound (I-1), 4-{[(6-bromopyrid-3-yl)methyl](2-fluoroethyl)amino}furan-2(5H)-one

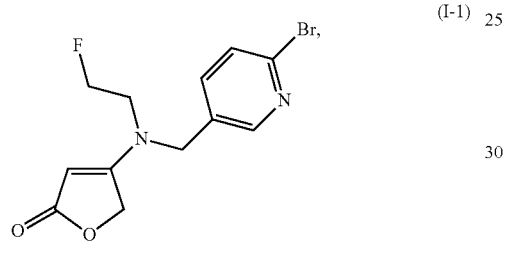
(I-1)

compound (I-2), 4-{[(6-fluoropyrid-3-yl)methyl](2,2-difluoroethyl)amino}furan-2(5H)-one

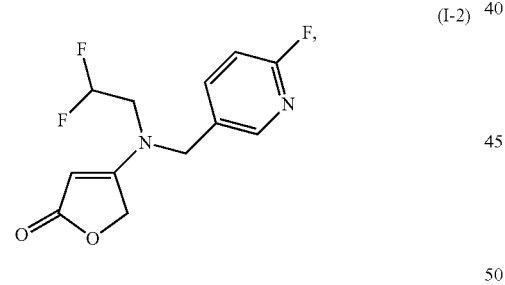
(I-2)

compound (I-3), 4-{[(2-chloro-1,3-thiazol-5-yl)methyl](2-fluoroethyl)amino}furan-2(5H)-one

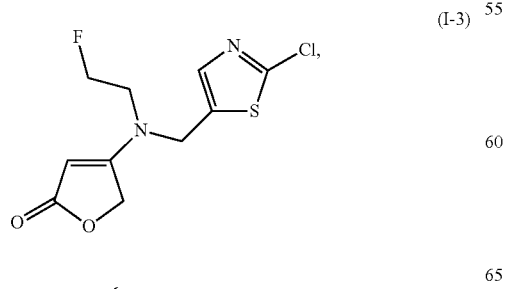
(I-3)

compound (I-4), 4-{[(6-chloropyrid-3-yl)methyl](2-fluoroethyl)amino}furan-2(5H)-one

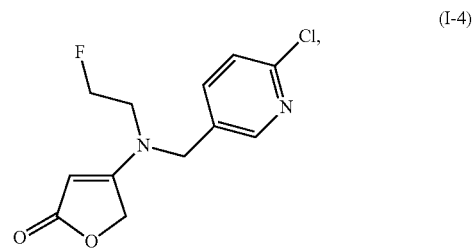 [SMILES: O=C1C=C(N(CCF)Cc2ccc(Br)nc2)CO1]
(I-4)

compound (I-5), 4-{[(6-chloropyrid-3-yl)methyl](2,2-difluoroethyl)amino}furan-2(5H)-one

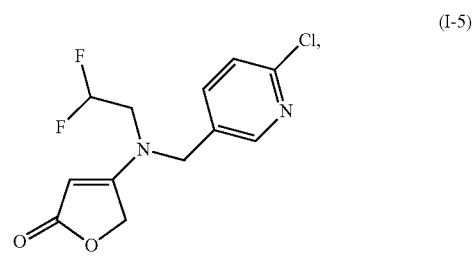 [SMILES: O=C1C=C(N(Cc2ccc(Cl)nc2)CC(F)F)CO1]
(I-5)

compound (I-6), 4-{[(6-chloro-5-fluoropyrid-3-yl)methyl](methyl)amino}furan-2(5H)-one

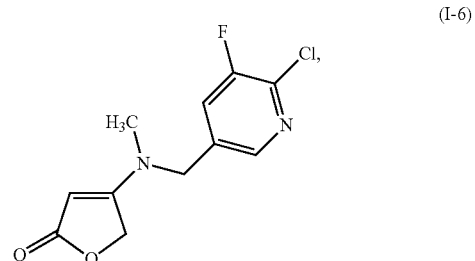
(I-6)

compound (I-7), 4-{[(5,6-dichloropyrid-3-yl)methyl](2-fluoroethyl)amino}furan-2(5H)-one

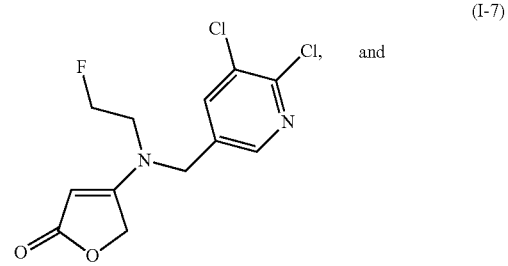 [SMILES: O=C1C=C(N(CCF)Cc2cnc(Cl)c(Cl)c2)CO1]
(I-7)

compound (I-8), 4-{[(6-chloro-5-fluoropyrid-3-yl)methyl](cyclopropyl)amino}furan-2(5H)-one

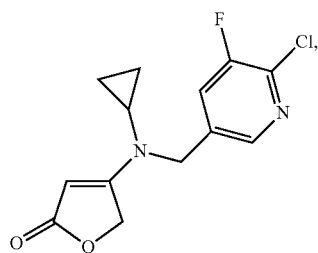
(I-8)

and at least one phthalic diamide compound selected from the group consisting of flubendiamide, (S)-3-iodo-N¹-{2-methyl-4-[1,2,2,2-tetrafluoro-1-(trifluoromethyl)ethyl]-phenyl}-N²-(1-methyl-2-methylsulphonylethyl)phthalamide,(S)-3-chloro-N¹-{2-methyl-4-[1,2,2,2-tetrafluoro-1-(trifluoromethyl)ethyl]phenyl}-N²-(1-methyl-2-methylsulphonyl-ethyl)phthalamide and (S)-3-bromo-N¹-{2-methyl-4-[1,2,2,2-tetrafluoro-1-(trifluoromethyl)ethyl]phenyl}-N²-(1-methyl-2-methylsulphonylethyl)phthalamide.

6. Method according to claim 2, comprising allowing the at least one compound and the at least one phthalic diamide compound to act on seed.

7. Method according to claim 2, comprising allowing the at least one compound and the at least one phthalic diamide compound to act on transgenic plants.

8. Method according to claim 2, comprising allowing the at least one compound and the at least one phthalic diamide compound to act on seed of transgenic plants.

9. Seed which has been treated with the at least one compound and the at least one phthalic diamide compound according to claim 2.

10. Seed according to claim 9 which has been treated simultaneously with the at least one compound and said at least one phthalic diamide compound.

11. Seed according to claim 9 which has been treated at different times with the at least one compound and said at least one phthalic diamide compound.

12. An active substance combination as defined in claim 1, wherein the at least one compound is selected from the group consisting of compound (I-4),

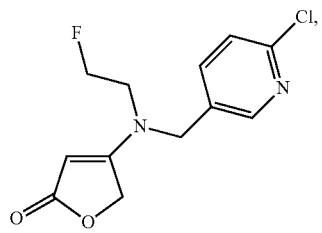
(I-4)

compound (I-5),

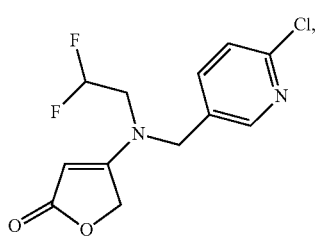
(I-5)

and compound (I-6)

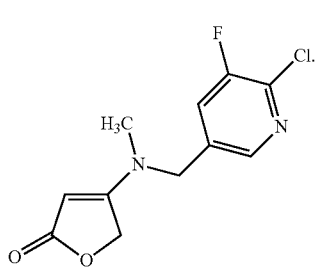
(I-6)

13. An active substance combination as defined in claim 1, wherein the at least one compound is compound (I-5)

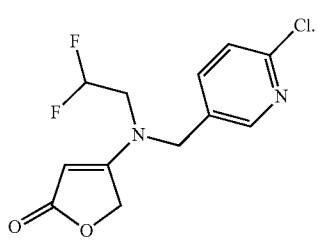
(I-5)

14. An active substance combination as defined in claim 1, wherein the at least one phthalic diamide compound is flubendiamide.

* * * * *